United States Patent
Swiderski

(10) Patent No.: US 10,538,761 B2
(45) Date of Patent: Jan. 21, 2020

(54) MULTIVALENT OLIGONUCLEOTIDE ASSEMBLIES

(71) Applicant: City of Hope, Duarte, CA (US)

(72) Inventor: Piotr Swiderski, San Dimas, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 15/209,545

(22) Filed: Jul. 13, 2016

(65) Prior Publication Data

US 2017/0029816 A1  Feb. 2, 2017

Related U.S. Application Data

(63) Continuation of application No. PCT/US2015/011172, filed on Jan. 13, 2015.
(Continued)

(51) Int. Cl.
*C12N 15/113* (2010.01)
*A61K 47/61* (2017.01)
(Continued)

(52) U.S. Cl.
CPC .......... *C12N 15/113* (2013.01); *C12N 15/111* (2013.01); *C12N 2310/14* (2013.01);
(Continued)

(58) Field of Classification Search
CPC ................ C12N 15/111; C12N 15/113; C12N 2310/351; C12N 2310/53; C12N 2330/00;
(Continued)

(56) References Cited

U.S. PATENT DOCUMENTS 6,159,694 A   12/2000  Karras
6,692,959 B2   2/2004  Bennett et al.
(Continued)

FOREIGN PATENT DOCUMENTS

WO   WO-2006/096754 A2   9/2006
WO   WO-2006/096754 A3   9/2006
(Continued)

OTHER PUBLICATIONS

Santulli-Marotto et al. Cancer Research (2003). vol. 63:7483-7489, Supplementary Methods and Supplementary Information provided.*
(Continued)

*Primary Examiner* — Terra C Gibbs
(74) *Attorney, Agent, or Firm* — Mintz, Levin, Cohn, Ferris, Glovsky and Popeo, P.C.

(57) ABSTRACT

Provided herein, inter alia, are double stranded oligonucleotide molecules and methods of making the molecules. The double stranded oligonucleotide molecules include a first oligonucleotide strand comprising a first nucleic acid sequence bound to a second nucleic acid sequence through a first spacer, wherein said second nucleic acid sequence is bound to a third nucleic acid sequence through a second spacer and a second oligonucleotide strand comprising a fourth nucleic acid sequence bound to a fifth nucleic acid sequence through a third spacer, wherein said fifth nucleic acid sequence is bound to a sixth nucleic acid sequence through a fourth spacer, wherein the second nucleic acid sequence and the fifth nucleic acid sequence are hybridized to form a double stranded nucleic acid core of said double stranded oligonucleotide.

19 Claims, 13 Drawing Sheets

Specification includes a Sequence Listing.

Related U.S. Application Data

(60) Provisional application No. 61/926,658, filed on Jan. 13, 2014.

(51) Int. Cl.

| A61K 31/7105 | (2006.01) |
|---|---|
| A61K 31/713 | (2006.01) |
| C07H 21/02 | (2006.01) |
| C12N 15/11 | (2006.01) |

(52) U.S. Cl.
CPC .... *C12N 2310/351* (2013.01); *C12N 2320/30* (2013.01); *C12N 2330/00* (2013.01)

(58) Field of Classification Search
CPC ........ A61K 47/55; A61K 47/64; A61K 47/61; A61K 47/549
USPC .............................................. 536/23.1, 24.5
See application file for complete search history.

(56) References Cited

U.S. PATENT DOCUMENTS

| 6,710,174 | B2 | 3/2004 | Bennett et al. |
|---|---|---|---|
| 8,748,408 | B2 | 6/2014 | Yu et al. |
| 9,688,982 | B2 | 6/2017 | Yu et al. |
| 2003/0060440 | A1 | 3/2003 | Klinman et al. |
| 2004/0097719 | A1 | 5/2004 | Agrawal et al. |
| 2004/0198685 | A1 | 10/2004 | Agrawal et al. |
| 2005/0130922 | A1 | 6/2005 | Altaba et al. |
| 2005/0256071 | A1 | 11/2005 | Davis |
| 2006/0019913 | A1 | 1/2006 | McSwiggen et al. |
| 2006/0127502 | A1 | 6/2006 | Yu et al. |
| 2008/0214436 | A1 | 9/2008 | Yu et al. |
| 2010/0151464 | A1 | 6/2010 | Stuelpnagel et al. |
| 2010/0298409 | A1 | 11/2010 | Xie et al. |
| 2011/0071210 | A1 | 3/2011 | Yu et al. |
| 2014/0066592 | A1 | 3/2014 | Glendora et al. |
| 2016/0222381 | A1 | 8/2016 | Lim |
| 2018/0142239 | A1 | 5/2018 | Yu et al. |

FOREIGN PATENT DOCUMENTS

| WO | WO-2007/143086 A2 | 12/2007 |
|---|---|---|
| WO | WO-2007/143086 A3 | 12/2007 |
| WO | WO-2012/128785 A1 | 9/2012 |

OTHER PUBLICATIONS

Chiu, Ya-Lin et al., "siRNA function in RNAi: A chemical modification analysis," RNA, vol. 9, No. 9, pp. 1034-1048, © 2003 RNA Society.

Chu, T.C. et al., "Aptamer Mediated siRNA Delivery," Nucleic Acids Research, Jan. 1, 2006, vol. 34, No. 10, E73 (pp. 1-6).

Hoene, V. et al., "Human momcyte-derived dendritic cells express TRL9 and react directly to the CpG-A oligonucleotide D19," Journal of Leukocyte Biology, vol. 80(6), Dec. 2006, pp. 1328-1336, © Society for Leukocyte Biology.

Maurer, T. et al., "CpG-DNA Aided Cross-Presentation of Soluble Antigens by Dendritic Cells, " European Journal of Immunology, Aug. 1, 2002, vol. 32, No. 8, pp. 2356-2364.

Santulli-Maratto, S. et al. (Nov. 2003). "Multivalent RNA aptamers that inhibit CTLA-4 and enhance tumor immunity," *Cancer Res* 63(21):7483-7489.

Kexiong Zhang et al., "Receptor-mediated delivery of siRNAs by tethered nucleic acid base-paired interactions," RNA (2008), vol. 14:577-583.

Marcin Kortylewski et al. Nature Biotechnology, vol. 27(10):925-932, Oct. 2009.

Vollmer et al., Oligonucleotides, 2004, vol. 14:23-31.

McNamara et al., Nature Biotechnology, 2006, vol. 24:1005-1015.

Nesterova et al., Clinical Cancer Research, 2005, vol. 11(16):5950-5955.

Scanlon, KJ, Current Pharmaceutical Biotechnology, 2004, vol. 5:415-420.

Kortylewski, M. et al., "Inhibiting Stat3 signaling in the hematopoietic system elicits multicomponent antitumor immunity," Nature Medicine, vol. 11, No. 12, 1314-1321, Dec. 2005.

Kortylewski, M. et al., "Targeting STAT3 affects melanoma on multiple fronts," Cancer and Metastasis Reviews, 24:315-327, 2005, © Springer Science and Business Media.

Li, Long-Cheung et al., "Small dsRNAs induce transcriptional activation in human cells," PNAS, Nov. 14, 2006, vol. 103, No. 46, pp. 17337-17342.

Kuwabara T. et al. (2005). "The NRSE smRNA specifies the fate of adult hippocampal neural stem cells," Nucleic Acids Symposium Series No. 49, pp. 87-88, © Oxford University Press.

Janowski, B.A.et al. (Mar. 2007, e-published Jan. 28, 2007). "Activating gene expression in mammalian cells with promoter-targeted duplex RNAs," Nature Chemical Biology, vol. 3, No. 3, Mar. 2007.

Yu, Hua et al. (Feb. 2004). "The Stats of Cancer—New Molecular Targets Come of Age," Nature Reviews, Cancer, vol. 4, Feb. 2004, © 2004 Nature Publishing Group.

Yu, Hua et al., (Jan. 2007). "Crosstalk between cancer and immune cells: role of STAT3 in the tumor microenvironment," Nature Reviews, Immunology, 7(1):41-51.

Check E. (Aug. 23, 2007). "Hitting the on switch," Nature 448(7156):855-858.

Morris, K.V. et al., "Small Interfering RNA-Induced Transcriptional Gene Silencing in Human Cells," Science, vol. 305, Aug. 27, 2004, pp. 1289-1292 and 14 supplemental pages.

Hammond, S.M., "Post-Transcriptional Gene Silencing by Double-Stranded RNA," Reviews, Feb. 2001, vol. 2, pp. 110-119, © 2001 Macmillan Magazines Ltd.

Furumoto, K. et al., "Induction of potent antitumor immunity by in situ targeting of intratumoral DCs," The Journal of Clinical Investigation, vol. 113, No. 5, Mar. 2004, pp. 774-783.

Hemmi, H. et al., "A Toll-like receptor recognizes bacterial DNA," Nature, vol. 408, Dec. 2000, pp. 740-745.

Kreig, A.M., "CpG motifs: the active ingredient in bacterial extracts?" Nature Medicine, vol. 9, No. 7, Jul. 2003, pp. 831-835.

Latz, E. et al., "TLR9 signals after translocating from the ER to CpG DNA in the lysosome," Nature Immunology, vol. 5, No. 2, Feb. 2004, pp. 190-198.

Vicari, A. P. et al. (Aug. 19, 2002). "Reversal of tumor-induced dendritic cell paralysis by CpG immunostimulatory oligonucleotide and anti-interleukin 10 receptor antibody," J. Exp. Med., vol. 196, No. 4, pp. 541-549.

Yasuda, K., "Endosomal translocation of vertebrate DNA activates dendritic cells via TRL9-dependent and -independent pathways," The Journal of Immunology, vol. 174, 2005, pp. 6129-6136.

Yu, D. et al., "'Immunomers'—novel 3'-3'-linked CpG oligodeoxyribonucleotides as potent immunomodulatory agents," Nucleic Acids Research, vol. 30, No. 20, 2002, pp. 4460-4469.

International Search Report dated Apr. 7, 2015, for PCT Application No. PCT/US2015/011172, filed Apr. 7, 2015, 4 pages.

Written Opinion dated Apr. 7, 2015, for PCT Application No. PCT/US2015/011172, filed Apr. 7, 2015, 5 pages.

International Search Report dated Mar. 26, 2012, for PCT Application No. PCT/US2011/051042, filed Mar. 26, 2012, 6 pages.

Written Opinion dated Mar. 26, 2012, for PCT Application No. PCT/US2011/051042, filed Mar. 26, 2012, 7 pages.

\* cited by examiner

MULTIVALENT OLIGONUCLEOTIDE ASSEMBLIES

CROSS-REFERENCE TO RELATED APPLICATION

This application is a continuation of PCT Application No. PCT/US2015/011172, filed Jan. 13, 2015, which claims priority to U.S. Provisional Application No. 61/926,658, filed Jan. 13, 2014, which are incorporated by reference herein in their entirety.

REFERENCE TO A "SEQUENCE LISTING," A TABLE, OR A COMPUTER PROGRAM LISTING APPENDIX SUBMITTED AS AN ASCII FILE

The Sequence Listing written in file 48440-519N01_ST25, created Oct. 5, 2016, 2,304 bytes, machine format IBM-PC, MS Windows operating system, is hereby incorporated by reference.

BACKGROUND OF THE INVENTION

Targeted drug delivery systems are a unique form of drug delivery where the pharmacologically active therapeutic agent is delivered only to its site of action and not to non-targeted sites. The goal of site specific drug delivery is to increase the selectivity and drug therapeutic index, and also to reduce the systemic toxicity of the drug. Therefore, targeted therapies provide a more promising alternative to circumvent the toxicities of conventional drugs, e.g., chemotherapeutic agents.

Various agents have been examined as targeting agents, including vitamins, carbohydrates, aptamers, peptides (e.g., Arg-Gly-Asp, allatostatin, transactivating transcriptional activator) and proteins (e.g., lectins, and transferrin). In addition, active agents, such as ligands for receptors and antibodies to surface proteins have been used extensively to target specific cells, but the majority of research to date has focused on antibodies.

Aptamers are DNA or RNA oligonucleotides that fold by intramolecular interaction into unique three dimensional conformations capable of binding to target antigens with high affinity and specificity. Aptamers exhibit many desirable properties for targeted drug delivery, such as ease of selection and synthesis, high binding affinity and specificity, low immunogenicity, and versatile synthetic accessibility. To date, a variety of anti-cancer agents (e.g. chemotherapy drugs, toxins, and siRNAs) have been successfully delivered to cancer cells in vitro using this technology. Aptamers possess several advantages over antibody ligands typically used in drug delivery. First, production of aptamers is easier to scale up with low batch-to-batch variability; second, aptamers are stable and can be denatured and renatured multiple times without loss of activity; third, the smaller size of aptamers relative to antibodies (~150 kDa) can lead to better tissue penetration in solid tumors; fourth, lack of immunogenicity is a major advantage of aptamers over antibodies; fifth, conjugation chemistry for the attachment of various imaging labels or functional groups to aptamers is orthogonal to nucleic acid chemistry, and functionality can be introduced during aptamer synthesis. On the other hand, the disadvantages of aptamers include faster excretion than antibodies due to smaller size, weaker binding to targets, toxicity and other systemic properties, and susceptibility to serum degradation.

Nanoparticles have also recently emerged as a strategy for delivering therapeutic molecules effectively to targeted sites. Nanoparticles conjugated to a targeting ligand for effective drug delivery increases the chance of binding to surface receptors. However, safer and more effective drug conjugates are still desired. Further, the ability to assemble a molecule consisting of various moieties performing various functions, would provide a level of freedom for modifying the most fundamental properties of therapeutic drugs. Provided herein are solutions for these and other needs in the art.

BRIEF SUMMARY OF THE INVENTION

Provided herein, inter alia, are double stranded oligonucleotide molecules including a first oligonucleotide strand comprising a first nucleic acid sequence bound to a second nucleic acid sequence through a first spacer, wherein said second nucleic acid sequence is bound to a third nucleic acid sequence through a second spacer and a second oligonucleotide strand comprising a fourth nucleic acid sequence bound to a fifth nucleic acid sequence through a third spacer, wherein said fifth nucleic acid sequence is bound to a sixth nucleic acid sequence through a fourth spacer, wherein the second nucleic acid sequence and the fifth nucleic acid sequence are hybridized to form a double stranded nucleic acid core of said double stranded oligonucleotide.

Also provided is a method of making a double stranded oligonucleotide molecule. The method includes the steps of attaching a first oligonucleotide strand to a substrate through a cleavable linker, said first oligonucleotide strand comprising a first nucleic acid sequence bound to a second nucleic acid sequence through a first spacer, wherein said second nucleic acid sequence is bound to a third nucleic acid sequence through a second spacer, and wherein said first nucleic acid sequence is bound to said cleavable linker, hybridizing a second oligonucleotide strand to said first oligonucleotide strand thereby forming a double stranded oligonucleotide, said second oligonucleotide strand comprising a fourth nucleic acid sequence bound to a fifth nucleic acid sequence through a third spacer, wherein said fifth nucleic acid sequence is bound to a sixth nucleic acid sequence through a fourth spacer, wherein the second nucleic acid sequence and the fifth nucleic acid sequence are hybridized to form a double stranded nucleic acid core of said double stranded oligonucleotide.

DETAILED DESCRIPTION OF THE INVENTION

Figure 1:
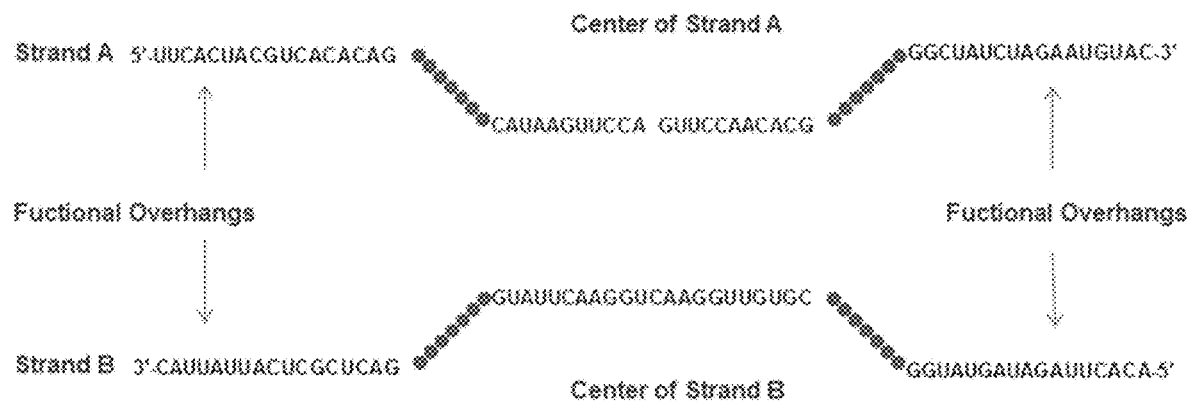
FIG. 1 is a schematic of an exemplary double stranded oligonucleotide molecule or tetravalent core provided herein containing two oligonucleotide strands, Strand A (SEQ ID NOS:1, 7 and 8, each separated by seven C3 spacers) and Strand B (SEQ ID NOS: 2, 9 and 10, each separated by seven C3 spacers). The centers of Strands A and B are complementary. Each Strand contains two functional nucleic acid overhangs separated from the center by a spacer or series of spacers.
Figure 2:
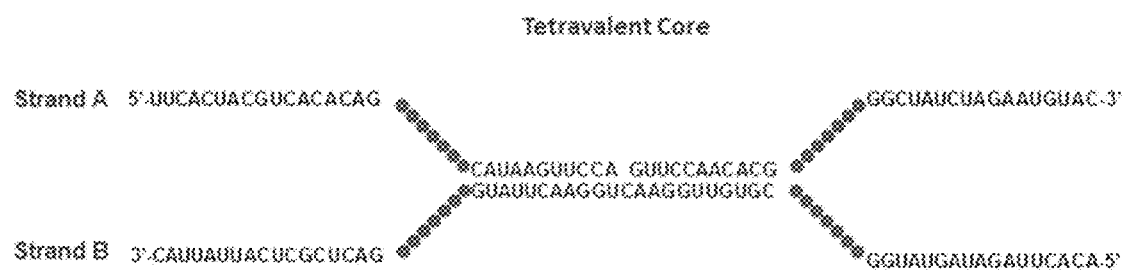
FIG. 2 is a schematic showing Strands A (SEQ ID NOS:1, 7 and 8, each separated by seven C3 spacers) and B (SEQ ID NOS: 2, 9 and 10, each separated by seven C3 spacers) annealed to each other to form an exemplary double stranded oligonucleotide or tetravalent core.

Provided herein, inter alia, are multifunctional, self-assembling, customizable double stranded oligonucleotide molecules and methods of making the molecules. The molecules are, optionally, used for targeted delivery of therapeutic agents. The oligonucleotide molecule contains a core, with four functional oligonucleotide overhangs attached to the core. The double stranded oligonucleotide molecule provided herein is alternatively referred to throughout as a tetrameric or tetravelent core. The terms tetrameric and tetravalent are used interchangeably. The core contains two partially complementary oligonucleotides, annealed with each other. See, e.g., FIGS. 1 and 2. After annealing, the interior or center sequences of the two strands of the core bind to each other, while the flanking parts of the sequence (i.e., functional overhangs) are single stranded. See, e.g., FIG. 2. The result is a core equipped with four short, single-stranded oligonucleotides. Moieties each equipped with a short oligonucleotide, complementary to one of the functional overhangs on the core structure, can be attached to the core by annealing of the short oligonucleotides to the complementary overhangs.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, and the like. Optionally, the nucleic acids herein contain phosphodiester bonds or linkages. In embodiments, nucleic acids comprise about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% phosphodiester linkages. In other embodiments, nucleic acid analogs are included that may have alternate backbones, comprising, e.g., phosphoramidate, phosphorothioate, phosphorodithioate, or O-methylphosphoroamidite linkages (see, e.g., Eckstein, Oligonucleotides and Analogues: A Practical Approach, Oxford University Press); and peptide nucleic acid backbones and linkages. Other analog nucleic acids include those with positive backbones, non-ionic backbones, and nonribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Thus, nucleic acids can comprise phosphodiester derivative linkages. Optionally, the nucleic acids comprise about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% phosphodiester derivative linkages. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments. Mixtures of naturally occurring nucleic acids and analogs can be made; alternatively, mixtures of different nucleic acid analogs, and mixtures of naturally occurring nucleic acids and analogs may be made.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., J. Biol. Chem. 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; and U.S. Pat. No. 5,143,854).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, a method using high affinity interactions may achieve the same results where one of a pair of binding partners binds to the other, e.g., biotin, streptavidin.

The terms "identical" or percent sequence "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site at ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. Employed algorithms can account for gaps and the like.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are wellknown in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively.

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent hybridization conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent hybridization conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al., John Wiley & Sons.

Nucleic acids may be substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

An "inhibitory nucleic acid" is a nucleic acid (e.g. DNA, RNA, polymer of nucleotide analogs) that is capable of binding to a target nucleic acid (e.g. an mRNA translatable into PTPRS) and reducing transcription of the target nucleic acid (e.g. mRNA from DNA) or reducing the translation of the target nucleic acid (e.g. mRNA) or altering transcript splicing (e.g. single stranded morpholino oligo). A "morpholino oligo" may be alternatively referred to as a "morphlino nucleic acid" and refers to morpholine-containing nucleic acid nucleic acids commonly known in the art (e.g. phosphoramidate morpholinio oligo or a "PMO"). See Marcos, P., Biochemical and Biophysical Research Communications 358 (2007) 521-527. In some embodiments, the "inhibitory nucleic acid" is a nucleic acid that is capable of binding (e.g. hybridizing) to a target nucleic acid (e.g. an mRNA translatable into an RPTPS) and reducing translation of the target nucleic acid. The target nucleic acid is or includes one or more target nucleic acid sequences to which the inhibitory nucleic acid binds (e.g. hybridizes). Thus, an inhibitory nucleic acid typically is or includes a sequence (also referred to herein as an "antisense nucleic acid sequence") that is capable of hybridizing to at least a portion of a target nucleic acid at a target nucleic acid sequence, An example of an inhibitory nucleic acid is an antisense nucleic acid. Another example of an inhibitory nucleic acid is siRNA or RNAi (including their derivatives or pre-cursors, such as nucleotide analogs). Further examples include shRNA, miRNA, shmiRNA, or certain of their derivatives or pre-cursors. In some embodiments, the inhibitory nucleic acid is single stranded. In other embodiments, the inhibitory nucleic acid is double stranded.

An "antisense nucleic acid" is a nucleic acid (e.g. DNA, RNA or analogs thereof) that is at least partially complementary to at least a portion of a specific target nucleic acid (e.g. a target nucleic acid sequence), such as an mRNA molecule (e.g. a target mRNA molecule) (see, e.g., Weintraub, Scientific American, 262:40 (1990)), for example antisense, siRNA, shRNA, shmiRNA, miRNA (microRNA). Thus, antisense nucleic acids are capable of hybridizing to (e.g. selectively hybridizing to) a target nucleic acid (e.g. target mRNA). In some embodiments, the antisense nucleic acid hybridizes to the target nucleic acid sequence (e.g. mRNA) under stringent hybridization conditions. In some embodiments, the antisense nucleic acid hybridizes to the target nucleic acid (e.g. mRNA) under moderately stringent hybridization conditions. Antisense nucleic acids may comprise naturally occurring nucleotides or modified nucleotides such as, e.g., phosphorothioate, methylphosphonate, and -anomeric sugar-phosphate, backbonemodified nucleotides. In some embodiments, an antisense nucleic acid is a morpholino oligo. In some embodiments, a morpholino oligo is a single stranded antisense nucleic acid, as is know in the art. In some embodiments, a morpholino oligo decreases protein expression of a target, reduces translation of the target mRNA, reduces translation initiation of the target mRNA, or modifies transcript splicing. In some embodiments, the morpholino oligo is conjugated to a cell permeable moiety (e.g. peptide). Antisense nucleic acids may be single or double stranded nucleic acids.

In the cell, the antisense nucleic acids may hybridize to the target mRNA, forming a double-stranded molecule. The antisense nucleic acids, interfere with the translation of the mRNA, since the cell will not translate a mRNA that is double-stranded. The use of antisense methods to inhibit the in vitro translation of genes is well known in the art (Marcus-Sakura, Anal. Biochem., 172:289, (1988)). Antisense molecules which bind directly to the DNA may be used.

Inhibitory nucleic acids can be delivered to the subject using any appropriate means known in the art, including by injection, inhalation, or oral ingestion. Another suitable delivery system is a colloidal dispersion system such as, for example, macromolecule complexes, nanocapsules, microspheres, beads, and lipid-based systems including oil-in-water emulsions, micelles, mixed micelles, and liposomes. An example of a colloidal system of this invention is a liposome. Liposomes are artificial membrane vesicles which are useful as delivery vehicles in vitro and in vivo. Nucleic acids, including RNA and DNA within liposomes and be delivered to cells in a biologically active form (Fraley, et al., Trends Biochem. Sci., 6:77, 1981). Liposomes can be targeted to specific cell types or tissues using any means known in the art. Inhibitory nucleic acids (e.g. antisense nucleic acids, morpholino oligos) may be delivered to a cell using cell permeable delivery systems (e.g. cell permeable peptides). In some embodiments, inhibitory nucleic acids are delivered to specific cells or tissues using viral vectors or viruses.

An "siRNA" refers to a nucleic acid that forms a double stranded RNA, which double stranded RNA has the ability to reduce or inhibit expression of a gene or target gene when the siRNA is present (e.g. expressed) in the same cell as the gene or target gene. The siRNA is typically about 5 to about 100 nucleotides in length, more typically about 10 to about 50 nucleotides in length, more typically about 15 to about 30 nucleotides in length, most typically about 20-30 base nucleotides, or about 20-25 or about 24-29 nucleotides in length, e.g., 20, 21, 22, 23, 24, 25, 26, 27, 28, 29, or 30 nucleotides in length. siRNA molecules and methods of generating them are described in, e.g., Bass, 2001, Nature, 411, 428-429; Elbashir et al., 2001, Nature, 411, 494-498; WO 00/44895; WO 01/36646; WO 99/32619; WO 00/01846; WO 01/29058; WO 99/07409; and WO 00/44914. A DNA molecule that transcribes dsRNA or siRNA (for instance, as a hairpin duplex) also provides RNAi. DNA molecules for transcribing dsRNA are disclosed in U.S. Pat. No. 6,573,099, and in U.S. Patent Application Publication Nos. 2002/0160393 and 2003/0027783, and Tuschl and Borkhardt, Molecular Interventions, 2:158 (2002).

The siRNA can be administered directly or siRNA expression vectors can be used to induce RNAi that have different design criteria. A vector can have inserted two inverted repeats separated by a short spacer sequence and ending with a string of T's which serve to terminate transcription.

Construction of suitable vectors containing the nucleic acid sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and re-ligated in the form desired.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, and the like. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (i.e., prostate, lymph node, liver, bone marrow, blood cell, joint tissue, synovial tissue, synoviocytes, fibroblast-like synoviocytes, macrophage-like synoviocytes, immune cells, hematopoietic cells, fibroblasts, macrophages, T cells, etc.), among other factors. Representative biopsy techniques include excisional biopsy, incisional biopsy, needle biopsy, surgical biopsy, and bone marrow biopsy. Biopsy techniques are discussed, for example, in Harrison's Principles of Internal Medicine, Kasper, et al., eds., 16th ed., 2005, Chapter 70, and throughout Part V.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3)

Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, Bioconjugate Techniques 1996, Academic Press, Inc., San Diego.

The term "recombinant" when used with reference, e.g., to a cell, or nucleic acid, protein, or vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761;

5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, and the like; or (b) the variable region, or a portion thereof, is altered, replaced or exchanged with a variable region having a different or altered antigen specificity. The preferred antibodies of, and for use according to the invention include humanized and/or chimeric monoclonal antibodies.

Techniques for conjugating therapeutic agents to antibodies are well known (see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The P388 leukemia model is widely accepted as being predictive of in vivo anti-leukemic activity. It is believed that a compound that tests positive in the P388 assay will generally exhibit some level of anti-leukemic activity in vivo regardless of the type of leukemia being treated. Accordingly, the present application includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, aleukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

As used herein, an "autoimmune disease" refers to a disease or disorder that arises from altered immune reactions by the immune system of a subject, e.g., against substances tissues and/or cells normally present in the body of the subject. Autoimmune diseases include, but are not limited to, arthritis, rheumatoid arthritis, psoriatic arthritis, juvenile idiopathic arthritis, scleroderma, systemic scleroderma, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, and allergic asthma.

As used herein, an "inflammatory disease" refers to a disease or disorder associated with abnormal or altered inflammation. Inflammation is a biological response initiated by the immune system as part of the healing process in response to a pathogen, damaged cells or tissues or irratants. Chronic inflammation can lead to a variety of diseases. Inflammatory diseases include, but are not limited to, atherosclerosis, allergies, asthma, rheumatoid arthritis, transplant rejection, celiac disease, chronic prostatitis, inflammatory bowel diseases, pelvic inflammatory diseases, and inflammatory myopathies.

As used herein, "metabolic disorders" refer to diseases or disorders involving abnormal metabolism of a variety of molecules and substances including, for example, caroby-drates, amino acids, organic acids. Metabolic disorders include, but are not limited to, disorders of carbohydrate metabolism, e.g., glycogen storage disease, disorders of amino acid metabolism, e.g., phenylketonuria, maple syrup urine disease, glutaric acidemia type 1, urea cycle disorder or urea cycle defects, e.g., carbamoyl phosphate synthetase I deficiency, disorders of organic acid metabolism (organic acidurias), e.g., alcaptonuria, disorders of fatty acid oxidation and mitochondrial metabolism, e.g., medium-chain acyl-coenzyme A dehydrogenase deficiency, disorders of porphyrin metabolism, e.g., acute intermittent porphyria, disorders of purine or pyrimidine metabolism, e.g., Lesch-Nyhan syndrome, disorders of steroid metabolism, e.g., lipoid congenital adrenal hyperplasia, congenital adrenal hyperplasia, disorders of mitochondrial function, e.g., Kearns-Sayre syndrome, disorders of peroxisomal function, e.g., Zellweger syndrome, and lysosomal storage disorders, e.g., Gaucher's disease, and Niemann Pick disease.

As used herein, "developmental disorders" refer to diseases or disorders often originating in childhood associated with language disorders, learning disorders, motor disorders and neurodevelopmental disorders. Examples include, but are not limited to, autism spectrum disorders and attention deficit disorders.

As used herein, "cardiovascular diseases" refer to diseases associated with the heart, blood vessels or both. Cardiovascular diseases include, but are not limited to, coronary heart disease, cardiomyopathy, hypertensive heart disease, heart failure, cardiac dysrhythmias, inflammatory heart disease, peripheral arterial disease, cerebrovascular disease and inflammatory heart disease.

As used herein, "liver diseases" refer to diseases associated with the abnormalities in the liver and/or liver function. Liver diseases include, but are not limited to, hepatitis, alcoholic liver disease, fatty liver disease, cirrhosis, Budd-Chiari syndrome, Gilbert's syndrome and cancer.

As used herein, the term "intestinal disease" refers to diseases or disorders associated with abnormalities in the intestine (small or large). Intestinal diseases include, but are not limited to, gastroenteritis, colitis, ileitis, appendicitis, coeliac disease, Chron's disease, enteroviruses, irritable bowel syndrome, and diverticular disease.

As used herein, the term "endocrine disease" refers to diseases or disorders of the endocrine system including endocrine gland hyposecretion, endocrine gland hypersecretion and tumors. Endocrine diseases include, but are not limited to, Addison's disease, diabetes, Conn's syndrome, Cushing's syndrome, glucocorticoid remediable aldosteronism, hypoglycemia, hyperthyroidism, hypothyroidism, thyroiditis, hypopituitarism, hypogonadism and parathyroid gland disorders.

As used herein, the term "neurological disorder" refers to diseases or disorders of the body's nervous system including structural, biochemical or electrical abnormalities. Neurological disorders include, but are not limited to, brain damage, brain dysfunction, spinal cord disorders, peripheral neuropathies, cranial nerve disorders, autonomic nervous system disorders, seizure disorders, movement disorders, e.g., Parkinson's disease and Multiple Sclerosis, and central neuropathies.

As used herein, the term "infectious disease" refers to diseases or disorders associate with infection, presence and/or growth of a pathogenic agent in a host subject. Infectious pathogenic agents include, but are not limited to, viruses, bacteria, fungi, protozoa, multicellular parasites and aberrant proteins, e.g., prions. Viruses associated with infectious disease include but are not limited to, herpes simplex viruses, cytomegalovirus, Epstein-Barr virus, Varicella-zoster virus, herpesviruses, Vesicular stomatitis virus, Hepatitis viruses, Rhinovirus, Coronavirus, Influenza viruses, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Simian Immunodeficiency viruses, Human Immunodeficiency viruses. Bacteria associated with infectious disease include, but are not limited to, *M. tuberculosis, Salmonella* species, *E. coli, Chlamydia* species, *Staphylococcus* species, *Bacillus* species, and *Pseudomonas* species.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

As used throughout, the terms "first," "second," "third," "fourth" and the like are used for clarity purposes and are not intended to be limiting unless specifically stated. Thus, for example, if a "second" nucleic acid sequence is annealed or hybridized to a "fifth" nucleic acid sequence, the terms "second" and "fifth" are used for clarity purposes and are not intended to define a specific feature of the nucleic acid, such as location or number, unless otherwise stated.

Provided herein are multifunctional, self-assembling, customizable double stranded oligonucleotide molecules. More specifically, provided herein are double stranded oligonucleotide molecules including a first oligonucleotide strand and a second oligonucleotide strand. The first oligonucleotide strand comprises a first nucleic acid sequence bound to a second nucleic acid sequence through a first spacer, wherein said second nucleic acid sequence is bound to a third nucleic acid sequence through a second spacer. The second oligonucleotide strand comprises a fourth nucleic acid sequence bound to a fifth nucleic acid sequence through a third spacer, wherein said fifth nucleic acid sequence is bound to a sixth nucleic acid sequence through a fourth spacer, wherein the second nucleic acid sequence and the fifth nucleic acid sequence are hybridized to form a double stranded nucleic acid core of said double stranded oligonucleotide. See, e.g., FIG. 2. Optionally, in the provided molecules, the first nucleic acid sequence, the third nucleic acid sequence, the fourth nucleic acid sequence and the sixth nucleic acid sequence are single stranded. Optionally, the nucleic acid sequences in the first, third, fourth and sixth nucleic acid sequences are the same. Optionally, the nucleic acid sequences in the first and sixth nucleic acid sequences are the same. Optionally, the nucleic acid sequences in the third and fourth nucleic acid sequences are the same.

The provided double stranded oligonucleotide molecules or tetravalent core can have one or more moieties attached to the core through the functional overhangs of the double stranded oligonucleotide molecule. See, e.g., FIG. 15. Thus, the provided oligonucleotide molecules, optionally, further comprise a first moiety attached to the first nucleic acid sequence of the first oligonucleotide. Optionally, the oligonucleotide further comprises a second moiety attached to the third nucleic acid sequence of the first oligonucleotide. Optionally, the oligonucleotide further comprises a third moiety attached to the fourth nucleic acid sequence of the second oligonucleotide. Optionally, the oligonucleotide further comprises a fourth moiety attached to the sixth nucleic acid sequence of the second oligonucleotide. Attachments of the moieties to the doubles stranded oligonucleotide or tetravalent core can be direct or indirect. Each of the first, second, third, and/or fourth moiety optionally comprises a single-stranded nucleic acid sequence, preferably a non-functional nucleic acid sequence that is complementary to one or more of the functional overhangs of the double stranded oligonucleotide or tetravalent core. Thus, optionally, the first moiety comprises a first moiety nucleic acid sequence hybridized to at least a portion of the first nucleic acid sequence of the double stranded oligonucleotide molecule. The second moiety can comprise a second moiety nucleic acid sequence hybridized to at least a portion of the third nucleic acid sequence of the double stranded oligo-nucleotide molecule. The third moiety can comprise a third moiety nucleic acid sequence hybridized to at least a portion of the fourth nucleic acid sequence of the double stranded oligonucleotide molecule. The fourth moiety can comprise a fourth moiety nucleic acid sequence hybridized to at least a portion of the sixth nucleic acid sequence of the double stranded oligonucleotide molecule.

Suitable moities for use in the provided oligonucleotide molecules and methods include, but are not limited to small molecules, antibodies, polypeptides and oligonucleotides. Thus, the first, second, third or fourth moiety can be a small molecule moiety, antibody moiety, polypeptide moiety or oligonucleotide moiety. Optionally, one or more of the first, second, third, or fourth moiety is a targeting moiety. Optionally, the targeting moiety is an antibody moiety, an aptamer moiety or a CpG oligodeoxynucleotide moiety. Optionally, one or more of the first, second, third, or fourth moiety is an active agent moiety. Optionally, the the active agent moiety is selected from the group consisting of a polypeptide moiety, an oligonucleotide moiety, a small molecule moiety or an antibody moiety. Optionally, the active agent moiety is a double-stranded nucleic acid moiety. Optionally, the double stranded moiety is an siRNA moiety. Optionally, the first and second moieties are active agent moieties and the third moiety is a targeting moiety. Optionally, the first and third moieties are active agent moieties and the second moiety is a targeting moiety.

Suitable spacers for use in the provided oligonucleotide molecules can be any spacer useful for linking two nucleic acid molecules. The spacers typically link a 5' phosphate of a nucleic acid base to a 3' phosphate of a nucleic acid base. Optionally, one or more of the spacers, e.g., the first, second, third and fourth spacers, are chemically identical. Thus, in the provided oligonucleotide molecules any combination of the first, second, third or fourth spacers can be chemically identical. Optionally, all the spacers, e.g., the first, second, third and fourth spacers, are the chemically identical. Optionally, all spacers are chemically distinct. The first, second, third and fourth spacers can be independently substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heterarylene. Optionally, the first, second, third and fourth spacers are independently substituted or unsubstituted alkylene, or substituted or unsubstituted heteroalkylene. Optionally, the first, second, third and fourth spacers are independently substituted or unsubstituted alkylene. Optionally, the first, second, third and fourth spacers are independently unsubstituted alkylene. Optionally, the first, second, third and fourth spacers are independently unsubstituted $C_1$-$C_{10}$ alkylene. Optionally, the first, second, third, and fourth spacers are phosphoramidate spacers, for example, from 3-10 carbon atoms such as a three carbon spacer or "C3 spacer." The C3 Spacer has a carbon backbone as illustrated in the following structure:

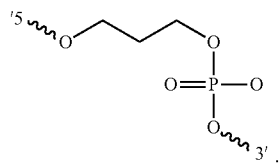

In embodiments, the spacer is a substituted or unsubstituted alkylphosphate spacer having the structure -$L^1$-($PO_4H$-$L^2$)$_n$-, wherein $L^1$ and $L^2$ are independently a substituted or unsubstituted alkylene (e.g. substituted or unsubstituted $C_1$-$C_{10}$ alkylene). In embodiments, wherein $L^1$ and $L^2$ are independently a unsubstituted alkylene (e.g. unsubstituted $C_1$-$C_{10}$ alkylene). In embodiments, wherein $L^1$ and $L^2$ are unsubstituted $C_3$ alkylene. In embodiments, $L^1$ and $L^2$ are the same. The symbol n is an integer from 1 to 500. In embodiments, n is an integer from 1 to 400. In embodiments, n is an integer from 1 to 300. In embodiments, n is an integer from 1 to 200. In embodiments, n is an integer from 1 to 100. In embodiments, n is an integer from 1 to 50. In embodiments, n is an integer from 1 to 25. In embodiments, n is an integer from 1 to 10. In embodiments, n is an integer from 1 to 5. In embodiments, n is an integer from 1 to 4. A person having ordinary skill in the art will recognize that the substituted or unsubstituted alkylphosphate spacer may exist in its salt form, e.g. $L^1$-($PO_4^-$-$L^2$)$_n$-. The substituted or unsubstituted alkylphosphate spacer may connect the 3' phosphate of a first nucleic acid to a 5' phosphate of a second nucleic acid as described herein. In embodiments, the spacer may be a —($CH_2CH_2CH_2$—$PO_4H$)$_n$—, wherein n is an integer between 1 and 20 (e.g., 1, 2, 3, 4, 5, 6, 7, 8, 9, 10, 11, 12, 13, 14, 15, 16, 17, 18, 19, or 20). In embodiments, the spacer may be a —($CH_2CH_2CH_2$—$PO_4H$)$_n$—, wherein n is an integer between 1 and 20 (e.g., 1, 2, 3, 4, 5, 6, 7, 8, 9, 10, 11, 12, 13, 14, 15, 16, 17, 18, 19, or 20) wherein the terminal spacer propyl moiety is bonded directly to a 3' phosphate moiety and the terminal spacer phosphate moiety is bonded directly to a 5' carbon of a deoxyribose. In embodiments, the spacer includes a phosphodiester linkage. Optionally, the spacer comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% phosphodiester linkages. In embodiments, the spacer includes a phosphodiester derivative linkage (e.g., phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, or O-methylphosphoroamidite linkage). In embodiments, the spacer includes a phosphodiester derivative (e.g., phosphoramidate, phosphorodiamidate, phosphorothioate, phosphorodithioate, phosphonocarboxylic acid, phosphonocarboxylate, phosphonoacetic acid, phosphonoformic acid, methyl phosphonate, boron phosphonate, and O-methylphosphoroamidite).

An example of a spacer or linker is shown below.

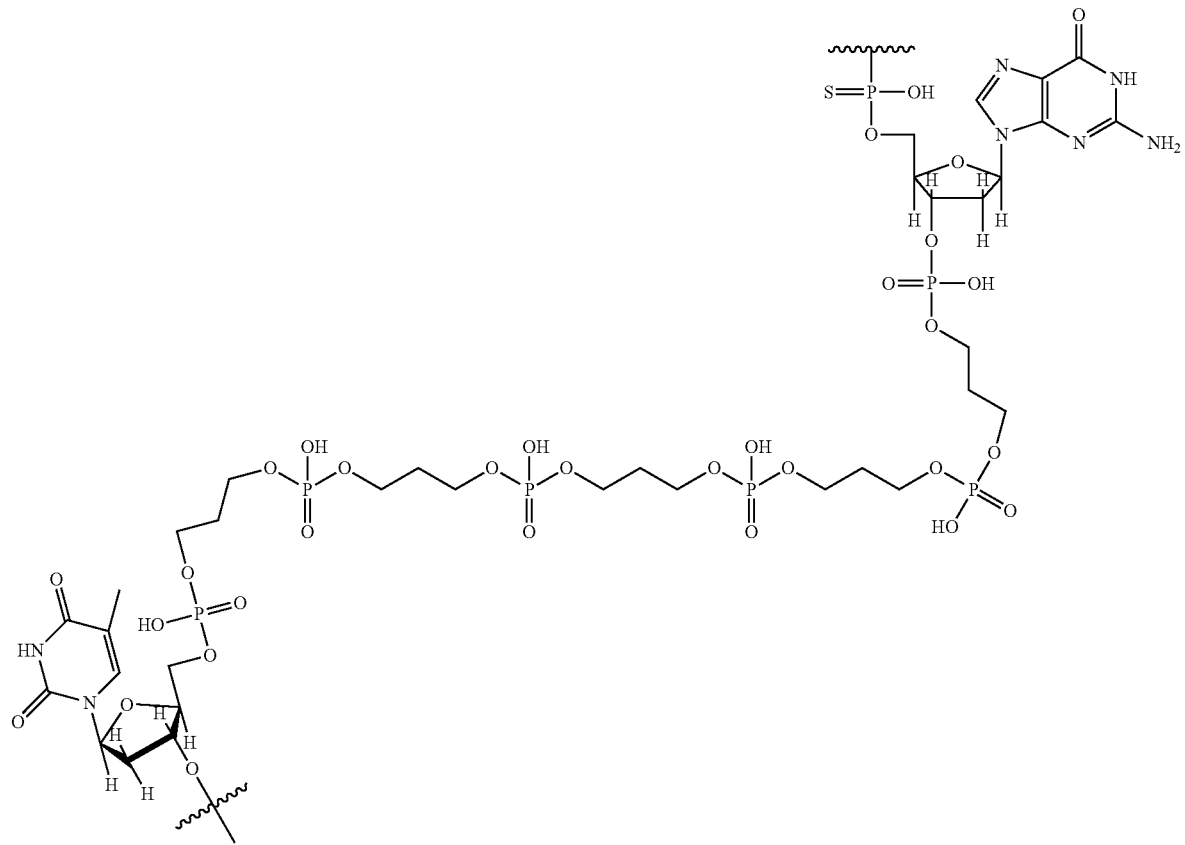

In embodiments, the phosphodiester linkage of the compound is replaced with a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages). In embodiments, a plurality of phosphodiester linkage of the compound are replaced with, phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof). In embodiments, a phosphorothioate linkage of the compound is replaced with a phosphodiester linkage or a different phosphodiester derivative linkage. In embodiments, a plurality of phosphorothioate linkages of the spacer are replaced with phosphodiester linkages or different phosphodiester derivative linkages. In embodiments, one or more linkages in the spacer is a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages), (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99%, or all spacer linkages are phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof)).

Also provided is a method of making a double stranded oligonucleotide molecule. The method including steps of attaching a first oligonucleotide strand to a substrate through a cleavable linker, said first oligonucleotide strand comprising a first nucleic acid sequence bound to a second nucleic acid sequence through a first spacer, wherein said second nucleic acid sequence is bound to a third nucleic acid sequence through a second spacer, and wherein said first nucleic acid sequence is bound to said cleavable linker, hybridizing a second oligonucleotide strand to said first oligonucleotide strand thereby forming a double stranded oligonucleotide, said second oligonucleotide strand comprising a fourth nucleic acid sequence bound to a fifth nucleic acid sequence through a third spacer, wherein said fifth nucleic acid sequence is bound to a sixth nucleic acid sequence through a fourth spacer, wherein the second nucleic acid sequence and the fifth nucleic acid sequence are hybridized to form a double stranded nucleic acid core of said double stranded oligonucleotide. Optionally, the first nucleic acid sequence, the third nucleic acid sequence, the fourth nucleic acid sequence and the sixth nucleic acid sequence are single stranded. Optionally, the nucleic acid sequences in the first, third, fourth and sixth nucleic acid sequences are the same. Optionally, the nucleic acid sequences in the first and sixth nucleic acid sequences are the same and/or the nucleic acid sequences in the third and fourth nucleic acid sequences are the same.

As used herein, the term "substrate" refers to any surface or support or collection of surfaces or supports to which nucleic acids can be attached. Suitable surfaces include, but are not limited to, beads, resins, gels, wells, columns, chips, flowcells, membranes, matrices, plates or filters. For example, the surface can be latex or dextran beads, polystyrene or polypropylene surfaces, polyacrylamide gels, gold surfaces, glass surfaces, optical fibers, or silicon wafers. The surface can be any material that amenable to chemical modification to afford covalent linkage to a nucleic acid.

Optionally, the method further includes attaching one or more moieties to the double stranded oligonucleotide. Thus, the method can include attaching a first moiety to the first nucleic acid sequence, attaching a second moiety to the third nucleic acid sequence, attaching a third moiety to the fourth nucleic acid sequence, and/or attaching a fourth moiety to the sixth nucleic acid sequence. Optionally, the first moiety comprises a first moiety nucleic acid sequence hybridized to at least a portion of the first nucleic acid sequence of the double stranded nucleic acid. Optionally, the second moiety comprises a second moiety nucleic acid sequence hybridized to at least a portion of the third nucleic acid sequence of the double stranded oligonucleotide molecule. Optionally, the third moiety comprises a third moiety nucleic acid sequence hybridized to at least a portion of the fourth nucleic acid sequence of the double stranded oligonucleotide molecule. Optionally, the fourth moiety comprises a fourth moiety nucleic acid sequence to at least a portion of the the sixth nucleic acid sequence of the double stranded oligonucleotide molecule.

As discussed above, one or more of the spacers can be chemically identical. Optionally, the first and second spacers are chemically identical. Optionally, the third and fourth spacers are chemically identical. Optionally, the first, second, third and fourth spacers are the chemically identical. Optionally, the first, second, third and fourth spacers are independently substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heterarylene. Optionally, the first, second, third and fourth spacers are independently substituted or unsubstituted alkylene, or substituted or unsubstituted heteroalkylene. Optionally, the first, second, third and fourth spacers are independently substituted or unsubstituted alkylene. Optionally, the first, second, third and fourth spacers are independently unsubstituted alkylene. Optionally, the first, second, third and fourth spacers are independently unsubstituted C1-C10 alkylene. Optionally, the first, second, third, and fourth spacers are phosphoramidate spacers, for example, from 3-10 carbon atoms such as a three carbon spacer or C3 spacer.

In embodiments, the spacer is a substituted or unsubstituted alkylphosphate spacer having the structure $-L^1-(PO_4H-L^2)_n-$, wherein $L^1$ and $L^2$ are independently a substituted or unsubstituted alkylene (e.g. substituted or unsubstituted alkylene). In embodiments, wherein $L^1$ and $L^2$ are independently a unsubstituted alkylene (e.g. unsubstituted $C_1-C_{10}$ alkylene). In embodiments, wherein $L^1$ and $L^2$ are unsubstituted $C_3$ alkylene. In embodiments, $L^1$ and $L^2$ are the same. The symbol n is an integer from 1 to 500. In embodiments, n is an integer from 1 to 400. In embodiments, n is an integer from 1 to 300. In embodiments, n is an integer from 1 to 200. In embodiments, n is an integer from 1 to 100. In embodiments, n is an integer from 1 to 50. In embodiments, n is an integer from 1 to 25. In embodiments, n is an integer from 1 to 10. In embodiments, n is an integer from 1 to 5. In embodiments, n is an integer from 1 to 4. A person having ordinary skill in the art will recognize that the substituted or unsubstituted alkylphosphate spacer may exist in its salt form, e.g. $L^1-(PO_4^--L^2)_n$. The substituted or unsubstituted alkylphosphate spacer may connect the 3' phosphate of a first nucleic acid to a 5' phosphate of a second nucleic acid as described herein. In embodiments, the spacer may be a —(CH$_2$CH$_2$CH$_2$—PO$_4$H)$_n$—, wherein n is an integer between 1 and 20 (e.g., 1, 2, 3, 4, 5, 6, 7, 8, 9, 10, 11, 12, 13, 14, 15, 16, 17, 18, 19, or 20). In embodiments, the spacer may be a —(CH$_2$CH$_2$CH$_2$—PO$_4$H)$_n$—, wherein n is an integer between 1 and 20 (e.g., 1, 2, 3, 4, 5, 6, 7, 8, 9, 10, 11, 12, 13, 14, 15, 16, 17, 18, 19, or 20) wherein the terminal spacer propyl moiety is bonded directly to a 3' phosphate moiety and the terminal spacer phosphate moiety is bonded directly to a 5' carbon of a deoxyribose. In embodiments, the spacer includes a phosphodiester linkage. Optionally, the spacer comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% phosphodiester linkages. In embodiments, the spacer includes a phosphodiester derivative linkage (e.g., phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, or O-methylphosphoroamidite linkage). In embodiments, the spacer includes a phosphodiester derivative (e.g., phosphoramidate, phosphorodiamidate, phosphorothioate, phosphorodithioate, phosphonocarboxylic acid, phosphonocarboxylate, phosphonoacetic acid, phosphonoformic acid, methyl phosphonate, boron phosphonate, and O-methylphosphoroamidite).

In the provided methods, the first oligonucleotide strand or second oligonucleotide strand is optionally covalently bound to the cleavable linker. Optionally, the cleavable linker comprises a nucleic acid sequence and the first oligonucleotide strand or second oligonucleotide strand is bound to the cleavable linker by hybridizing at least a portion of the first or second oligonucleotide strand to at least a portion of the cleavable linker nucleic acid sequence. Optionally, the method further comprises cleaving the cleavable linker to release the first or second oligonucleotide strand from the substrate. In the method of making the double stranded oligonucleotide molecule cleavage of the cleavable linker can occur prior to addition of any of the moities or after addition of any one of the moities. Thus, cleavage can occur prior to attaching a moiety to the double stranded oligonucleotide molecule or after attachment of the first, second, third or fourth moiety. Optionally, cleavage occurs prior to attaching the fourth moiety to the sixth nucleic acid sequence of the double stranded oligonucleotide molecule.

Cleavable linkers and methods of cleaving the linkers are known and can be employed in the provided methods using the knowledge of those of skill in the art. For example, the cleavable linker can be cleaved by an enzyme, a catalyst, a chemical compound, temperature, electromagnetic radiation or light. Optionally, the cleavable linker comprises a moiety hydrolysable by beta-elimination, a moiety cleavable by acid hydrolysis, a enzymatically cleavable moiety, or a photo-cleavable moiety.

As discussed above, suitable moieties for use in the provided oligonucleotide molecules and methods include, but are not limited to small molecules, antibodies, polypeptides and oligonucleotides. Thus, the first, second, third or fourth moiety can be a small molecule moiety, antibody moiety, polypeptide moiety or oligonucleotide moiety. Optionally, one or more of the first, second, third, or fourth moiety is a targeting moiety. Optionally, the targeting moiety is an antibody moiety, an aptamer moiety or a CpG oligodeoxynucleotide moiety. Optionally, one or more of the first, second, third, or fourth moiety is an active agent moiety. Optionally, the the active agent moiety is selected from the group consisting of a polypeptide moiety, an oligonucleotide moiety, a small molecule moiety or an antibody moiety. Optionally, the active agent moiety is a double-stranded nucleic acid moiety. Optionally, the double stranded moiety is an siRNA moiety. Optionally, the first and second moieties are active agent moieties and the third moiety is a targeting moiety. Optionally, the first and third moieties are active agent moieties and the second moiety is a targeting moiety.

The double stranded oligonucleotide molecules containing at least one active agent moiety and compositions comprising the double stranded oligonucleotide molecules are useful for both prophylactic and therapeutic treatment. For prophylactic use, a therapeutically effective amount of the agents described herein are administered to a subject prior to or during early onset (e.g., upon initial signs and symptoms of an autoimmune disease). Therapeutic treatment involves administering to a subject a therapeutically effective amount of the agents described herein after diagnosis or development of disease.

Thus, provided is a method of treating a disease in a subject comprising administering to the subject an effective amount of a double stranded oligonucleotide molecule comprising at least one active agent moiety or composition comprising a double stranded oligonucleotide molecule comprising at least one active agent moiety as described herein. Administration of the molecule comprising the active agent moiety treats the disease or one or more symptoms of the disease in the subject.

Optionally, the methods of treatment includes administering to the subject a double stranded oligonucleotide molecule comprising an active agent moiety and a targeting moiety. Optionally, the method includes administration of a double stranded oligonucleotide molecule comprising more than one active agent moiety and, optionally, a targeting moiety. Optionally, the disease is selected from the group consisting of autoimmune disease, developmental disorder, inflammatory disease, metabolic disorder, cardiovascular disease, liver disease, intestinal disease, infectious disease, endocrine disease, neurological disorder, and cancer. Optionally, the disease is cancer.

In the provided methods of treatment, additional therapeutic agents can be used that are suitable to the disease being treated. Thus, in some embodiments, the provided methods of treatment further comprise administering a second therapeutic agent to the subject. Suitable additional therapeutic agents include, but are not limited to, therapeutic agent is selected from the group consisting of analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

According to the methods provided herein, the subject is administered an effective amount of one or more of the agents provided herein. The terms effective amount and effective dosage are used interchangeably. The term effective amount is defined as any amount necessary to produce a desired physiologic response (e.g., reduction of inflammation). Effective amounts and schedules for administering the agent may be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

Provided herein are kits comprising one or more of the provided nucleic acids and/or compositions and instructions for use. Thus, provided are kits comprising the double stranded oligonucleotide molecules or tetravalent core molecules or pharmaceutical compositions comprising the molecules and instructions for use. Optionally, the kits comprise the first and second oligonucleotide strands of the double stranded oligonucleotide molecule in one or separate containers. Optionally, the kits include the double stranded oligonucleotide molecules with one, two, three, or four moieties attached to the molecules. Optionally, the moieties and double stranded oligonucleotide molecules are in one or separate containers. Thus, for example, a provided kit can include, in separate containers, the double stranded oligonucleotide molecules, a first moiety, a second moiety, a third moiety and a fourth moiety. Optionally, the provided kits comprise a double stranded oligonucleotide molecule comprising a targeting moiety and an active agent for treatment of a disease. Optionally, the kit comprises one or more additional agents for treating or preventing one or more symptoms of a disease. Optionally, the kit comprises a means of administering the composition, such as, for example, a syringe, needle, tubing, catheter, patch, and the like. The kit may also comprise formulations and/or materials requiring sterilization and/or dilution prior to use.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims.

EXAMPLES

Example 1. Multifunctional Self-Assembling Oligonucleotide-Based Molecules for Drug Delivery Described herein, inter alia, are multifunctional, self-assembling, customizable double stranded oligonucleotide molecules, e.g., for targeted delivery of therapeutic agents. The oligonucleotide molecule contains a core, with four functional oligonucleotide overhangs attached to the core. The core is sometimes referred to herein as a tetrameric or tetravalent core. The terms tetrameric and tetravalent are used interchangeably. The core contains two partially complementary oligonucleotides, annealed with each other. See, e.g., FIGS. 1 and 2. After annealing, the interior or center sequences of the two strands of the core bind to each other, while the flanking parts of the sequence (i.e., functional overhangs) are single stranded. See, e.g., FIG. 2. The result is a core equipped with four short, single-stranded oligonucleotides. Moieties equipped with a short oligonucleotide, complementary to one of the functional overhangs on the core structure, can be attached to the core by annealing of the complementary nucleic acid molecules.

Oligonucleotides used as the components of the tetrameric core were synthesized on the Oligopilot10 plus, (GE, Piscataway Township, N.J.), automated synthesizer using standard phosphoramidite chemistry (Caruthers, *Acc. Chem. Res.* 24:278-84 (1991)). Phosphoramidites were purchased from Thermo Fisher Scientific (Milwaukee, Wis.), and solid supports from GE (Piscataway Township, N.J.). Oxidizer 0.05M Iodine in pyridine-water (v/v 9:1), Deblock 5% DCA in toluene, Activator 0.5M ETT and capping reagents were purched from AIC (Framingham, Mass.). HPLC system was purchased from Gilson, Inc. (Middleton, Wis.). All other chemicals were purchased from Sigma-Aldrich Corp. (St. Louis, Mo.). Oligonucleotide purification PRP-HPLC preparative columns were purchased from Hamilton (Reno, Nev.).

Synthesis of oligonucleotides was carried out as follows. Primer200 supports carrying 2'-OMe nucleosides, 2'-OMe phosphoramidites, 2'-Fluoro phosphoramidites and C3-Linker phosphoramidite were used for the synthesis of the oligonucleotides used as components of the tetrameric core. Synthesis was carried out at the 10 µM scale. After the synthesis was completed oligos were deprotected with the use of standard deprotection procedures. Purifications were performed by Ion-Pairing HPLC (Swiderski et al., *Anal. Biochem.* 216(1):83-8 (1994)), in 50 mM tetrabutylammonium acetate buffers, in acetonitrile gradient 10-90%, on HPLC column PRP-1 12-20 µm 100 Å 21.2×250 mm. Purity was confirmed by analytical, 8M urea, 20% PAGE and by analytical IE-FPLC on SOURCE 15Q 4.6/100 PE Ion Exchange Column from GE (Piscataway Township, N.J.).

Design of the components of the multifunctional, self-assembling, double stranded oligonucleotide molecules was carried out as follows. As noted above, the oligonucleotide molecules contain a core with four functional overhangs. The tetravalent core is made up of two oligonucleotide strands, Strand A and Strand B. Each of Strand A and Strand B consists of a center oligonucleotide and of an overhang on both ends of the center oligonucleotide. See FIG. 1. The center oligonucleotide is separated from the functional overhangs by the series of spacer or linker molecules, e.g., C3 spacers. The center oligonucleotides of Strand A and Strand B are fully complementary. Strand A and Strand B must anneal properly in order to create a tetravalent core. Therefore, the sequences of Strand A and Strand B were designed to minimize their potential for annealling into incorrect higher order structures. The RNA Folding algorithm (Sinha et al., *Mol. Cancer Ther.* 5:1909-1917 (2006)) and IDT's OligoAnalyzer 3.1 were used to design Strands A and B. Guidelines for selecting Strands A and B of the double stranded oligonucleotide molecule include rejecting strands if the core oligonucleotides present secondary structures, such as stable hairpins, rejecting strands if the core oligonucleotides present stable self-complementary structures, and rejecting strands if the functional overhangs (e.g., SE1, SE2, SE3, and SE4 shown in FIG. 3) interact with each other or if the functional overhangs (SE1, SE2, SE3, SE4) form stable self-complementary structures. With these rules, an exemplary multifunctional, self-assembling, oligonucleotide molecule was designed containing Strand A and B each with a 22 base pair core and two 17 base pair overhangs, separated from the core by a series of seven C3 spacers. Strand A and B each contain 70 base pairs. See FIGS. 1-3. Specifically, Strand A has the sequence 5'-UUCACUAC-GUCACACAGooooooo CAUAAGUUCCAGUUC-CAACACGooooooooGGCUAUCUAGAAUGUAC-3' (Sequences: UUCACUACGUCACACAG [SEQ ID NO:1]; CAUAAGUUCCAGUUCCAACACG [SEQ ID NO:7]; GGCUAUCUAGAAUGUAC [SEQ ID NO:8]) and Strand B has the sequence 5'-ACACUUAGAUAGUAUG-GoooooooCGUGUUGGAACUGGAACUUAU-GoooooooGACUC GCUCAUUAUUAC-3' (Sequences: ACACUUAGAUAGUAUGG [SEQ ID NO:2]; CGU-GUUGGAACUGGAACUUAUG [SEQ ID NO:9]; GACUCGCUCAUUAUUAC [SEQ ID NO:10]) with the "o" representing the C3 spacer.

Figure 3:
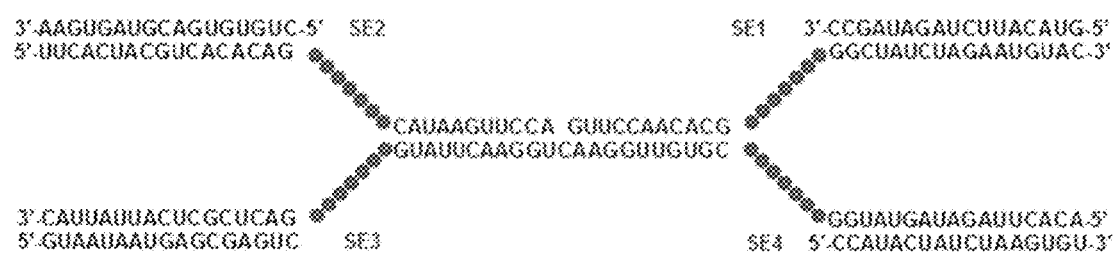
FIG. 3 is a schematic showing an exemplary tetravalent core with four non-functional oligonucleotides, SE1 (SEQ ID NO:3), SE2 (SEQ ID NO:4), SE3 (SEQ ID NO:5) and SE4 (SEQ ID NO:6) annealed to the four functional nucleic acid overhangs of the core comprising Strands A (SEQ ID NOS:1, 7 and 8, each separated by seven C3 spacers) and B (SEQ ID NOS: 2, 9 and 10, each separated by seven C3 spacers).

Nucleic acid strands complementary to the functional overhangs on Strands A and B were designed as follows and are shown in FIG. 3; specifically, 5'-GUA CAU UCU AGA UAG CC-3' (SEQ ID NO:3) 3LSE-4StrandA SE1, 5'-CUG UGU GAC GUA GUG AA-3' (SEQ ID NO:4) 5RSE-4StrandA SE2, 5'-GUA AUA AUG AGC GAG UC-3' (SEQ ID NO:5) 3LSE-4StrandB SE3, and 5'-CCA UAC UAU CUA AGU GU-3' (SEQ ID NO:6) 5RSE-4StrandB SE4.

The estimated level of interactions between the nucleic acid strands and the functional overhangs is shown in Table 1.

TABLE 1

Estimated level of interactions between the nucleic acid strands and the functional overhangs on Strands A and B.
Energy kcal/mol

|  | SE1 | SE2 | SE3 | SE4 |
|---|---|---|---|---|
| SE1 | −6.30 | −3.52 | −5.37 | −5.61 |
|  | −1.60 | −3.30 | −3.42 | −3.52 |
|  | −1.34 | −3.30 | −3.14 | −3.30 |
| SE2 | −3.52 | −7.31 | −3.61 | −3.90 |
|  | −3.30 | −3.65 | −1.60 | −1.95 |
|  | −3.30 | −3.14 | −1.60 | −1.95 |
| SE3 | −5.37 | −3.61 | −3.61 | −5.19 |
|  | −3.42 | −1.60 | −3.14 | −2.44 |
|  | −3.14 | −1.60 | −1.57 | −1.95 |
| SE4 | −5.61 | −3.90 | −5.19 | −2.94 |
|  | −3.52 | −1.95 | −2.44 | −2.44 |
|  | −3.30 | −1.95 | −1.95 | −1.95 |

Figure 4:
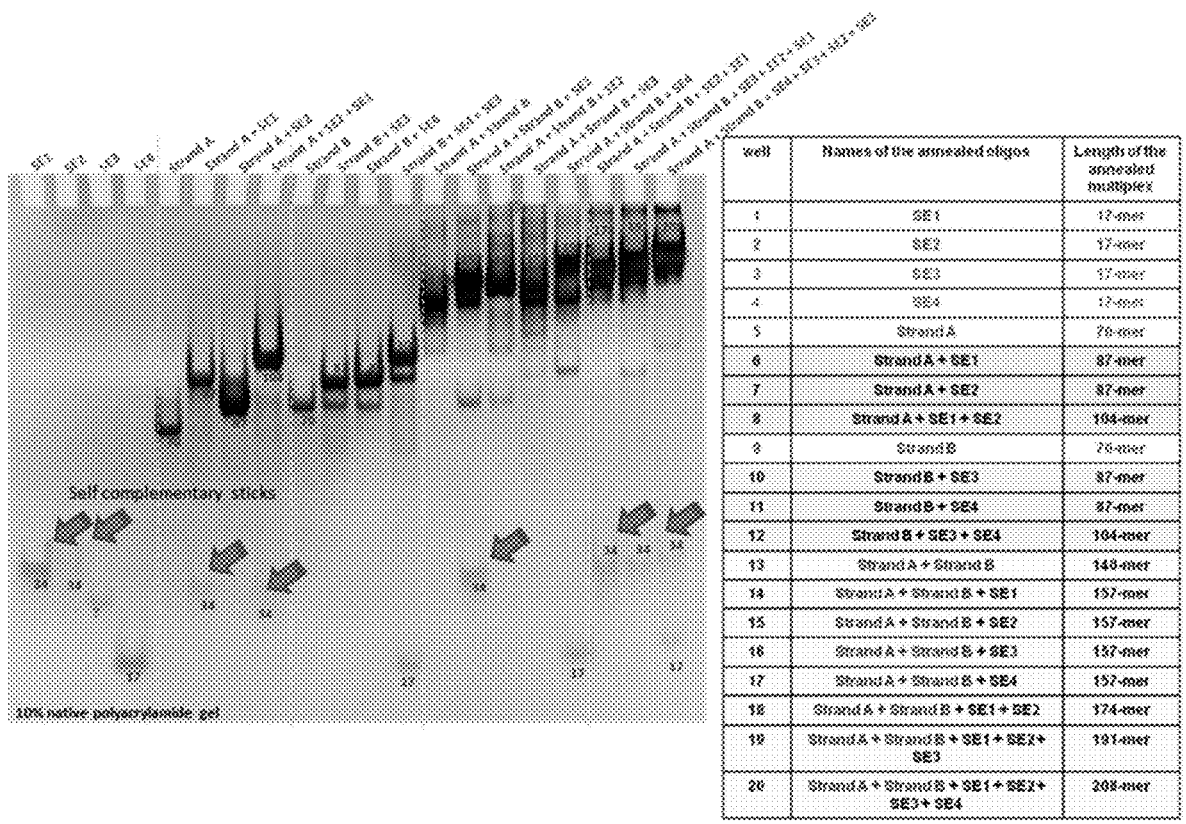
FIG. 4 is a picture of a gel showing the products of annealing of each of the parts of the double stranded oligonucleotide or tetravalent core strands with the four non-functional oligonucleotides in various combinations as shown in the table.

Components of the multifunctional oligonucleotide, i.e., strands A and B were annealed with other components, i.e., SE1, SE2, SE3 and SE4 in various combinations. The results are shown in FIG. 4. As seen from FIG. 4, some homodimers of SE1 and SE2 were visible in line 1 and line 2. However, FIG. 4 shows that sequential annealing of the core with the four non-functional overhangs (SE1, SE2, SE3, and SE4) resulted in the assembly of a multifunctional, self-assembling, customizable double stranded oligonucleotide molecule.

Figure 5:
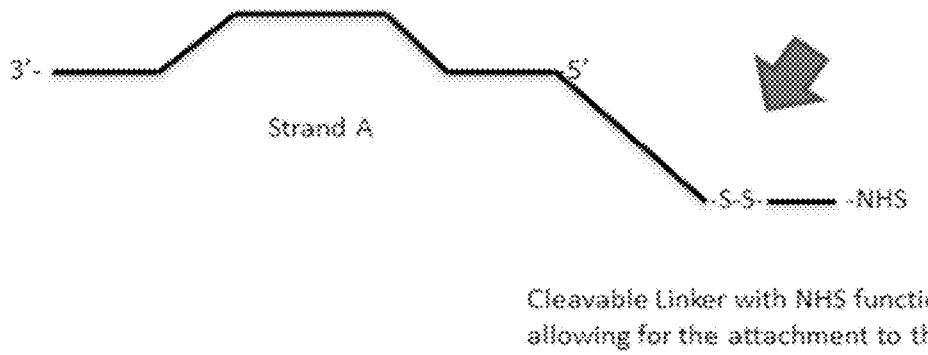
FIG. 5 is a schematic showing an exemplary first strand (Strand A) of an exemplary double stranded oligonucleotide or tetravalent core with a cleavable linker.
Figure 6:
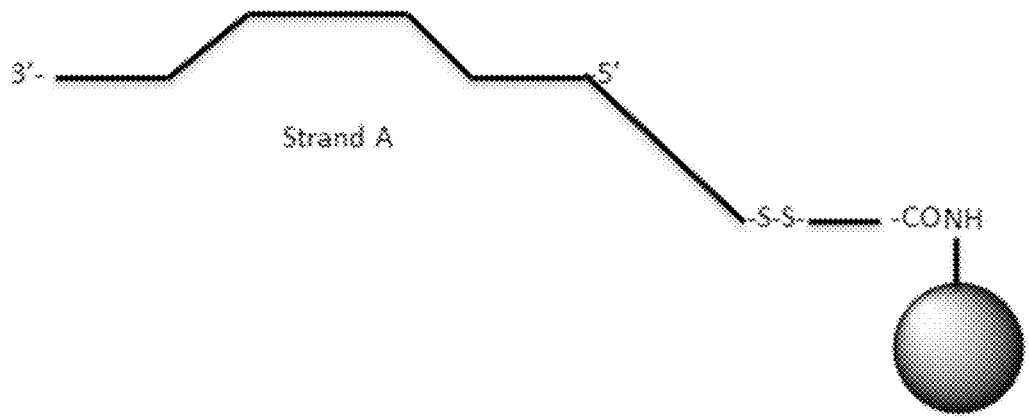
FIG. 6 is a schematic showing an exemplary first strand (Strand A) of an exemplary double stranded oligonucleotide or tetravalent core attached to a solid support, e.g., a bead, through the cleavable linker.
Figure 7:
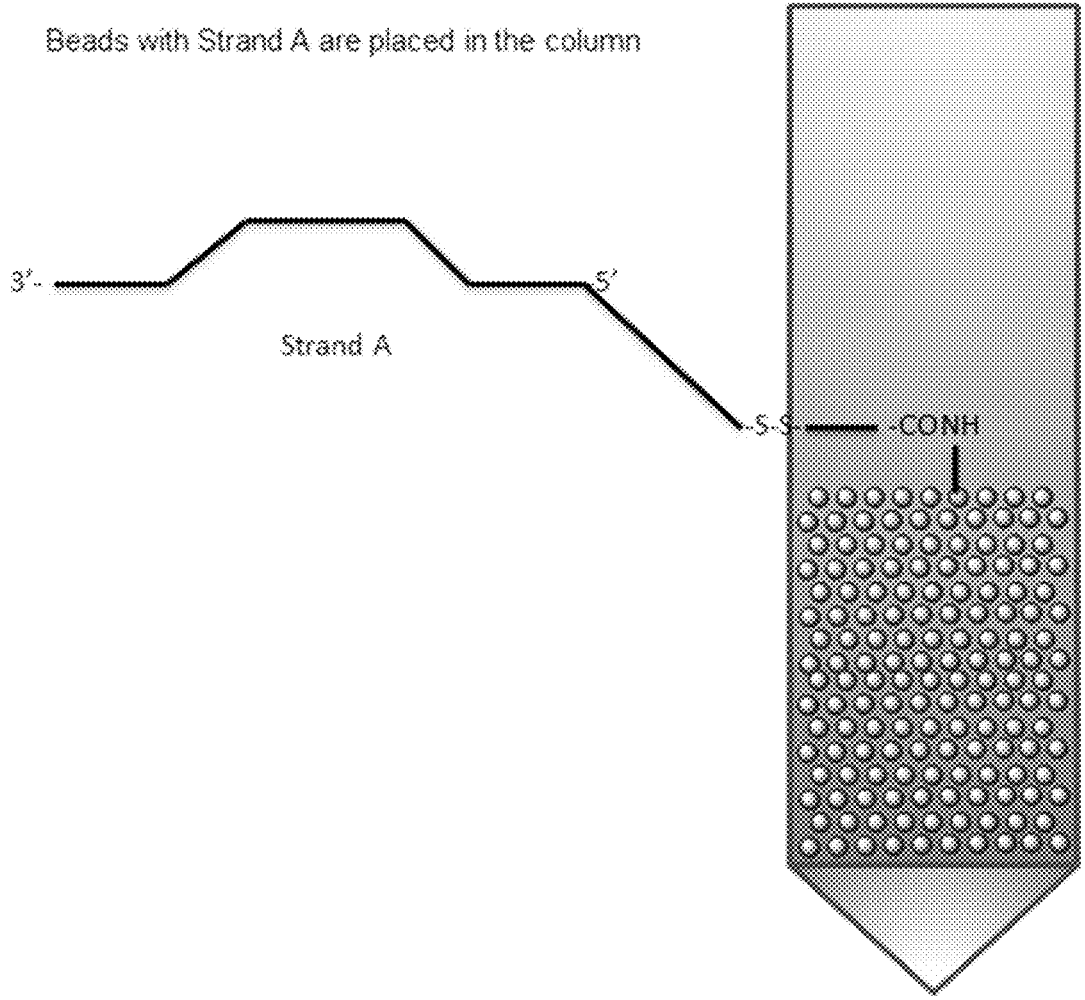
FIG. 7 is a schematic showing a column containing a multitude of beads each of which has attached first strands (Strand A) of an exemplary double stranded oligonucleotide or tetravalent core.
Figure 8:
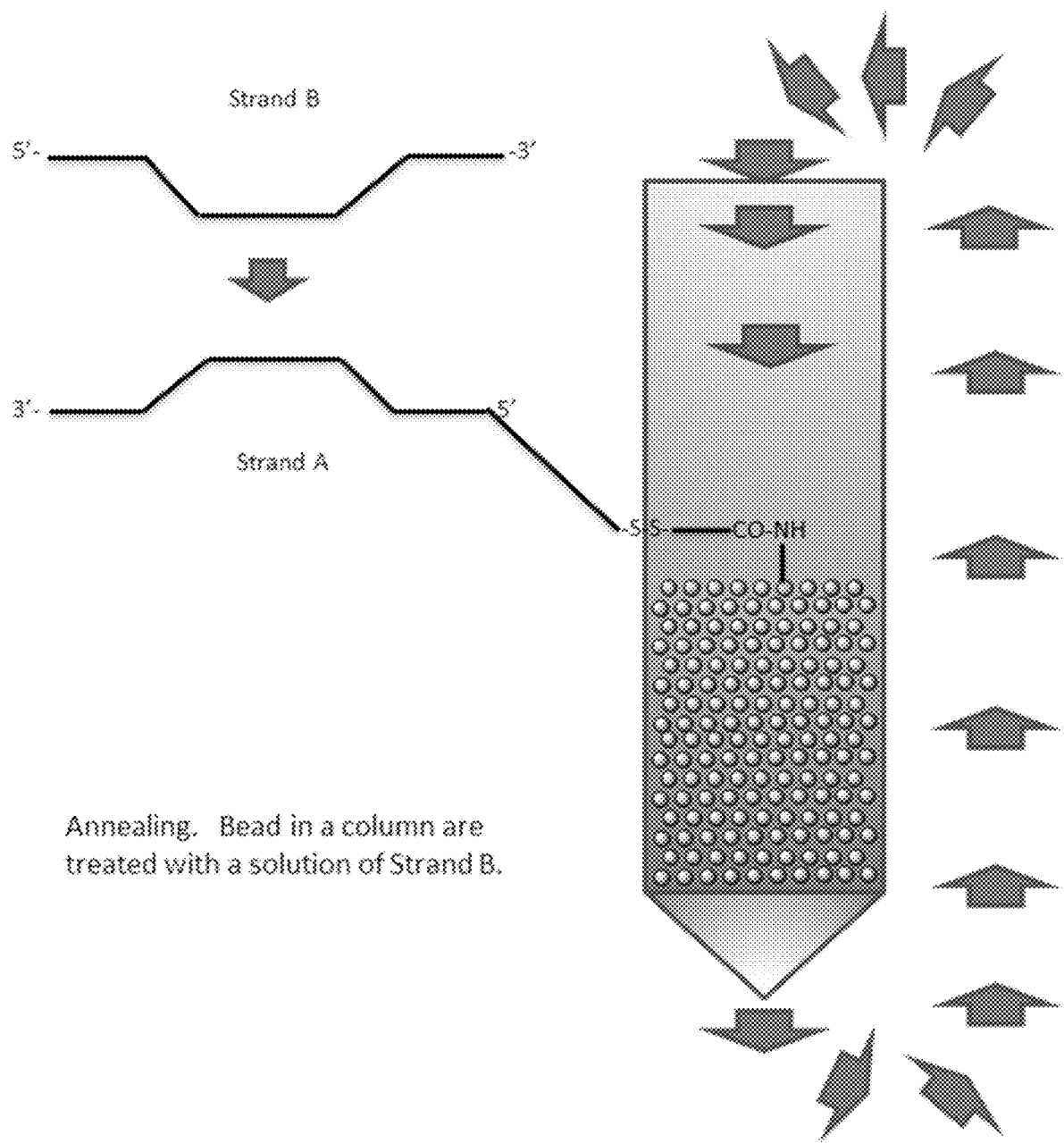
FIG. 8 is a schematic showing the annealing of the second strand (Strand B) of an exemplary double stranded oligonucleotide or tetravalent core to the first strand (Strand A).
Figure 9:
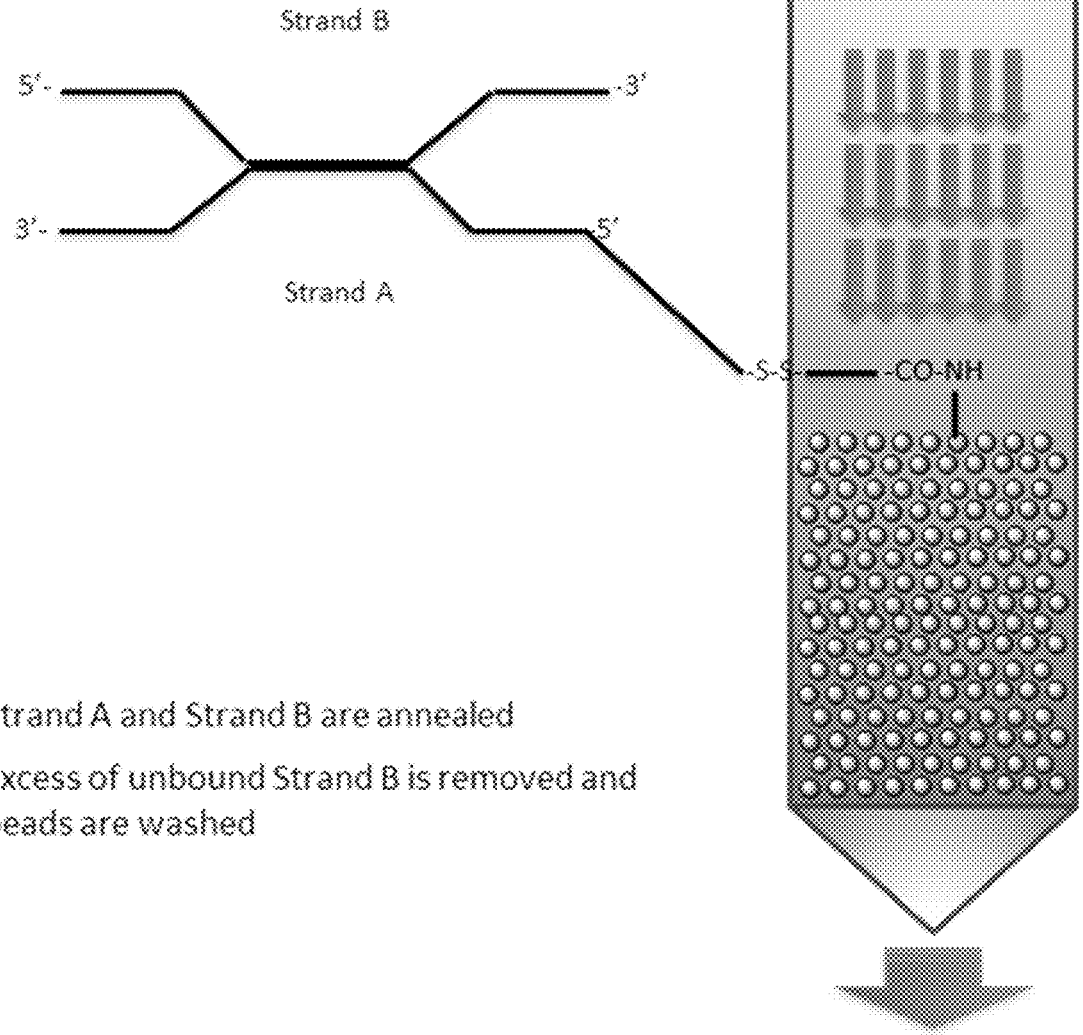
FIG. 9 is a schematic showing the washing of the column containing the beads each of which has a tetravalent core of annealed first and second strands (Strands A and B).
Figure 10:
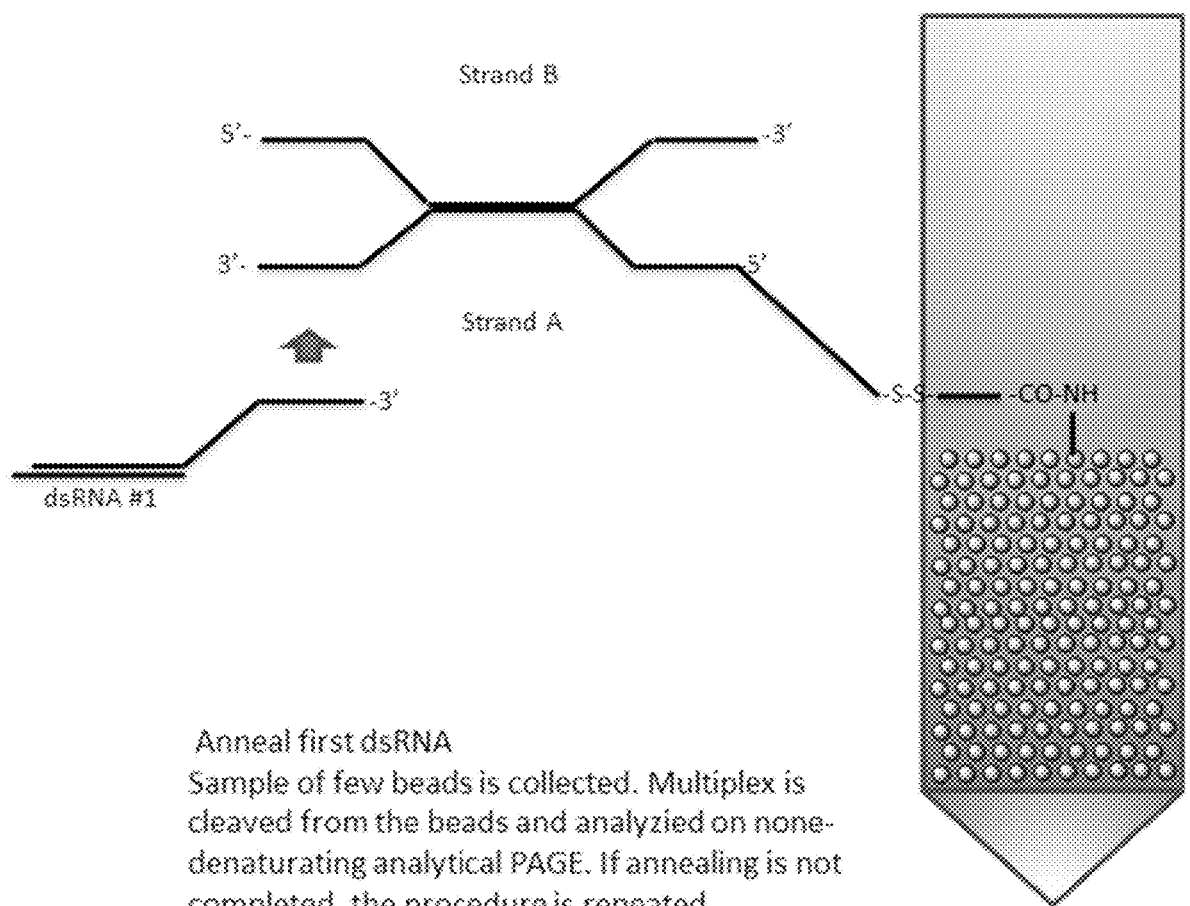
FIG. 10 is a schematic showing the annealing of a first moiety to an exemplary double stranded oligonucleotide or tetravalent core through the nucleic acid overhang on the first moiety to the first functional overhang on the tetravalent core.
Figure 11:
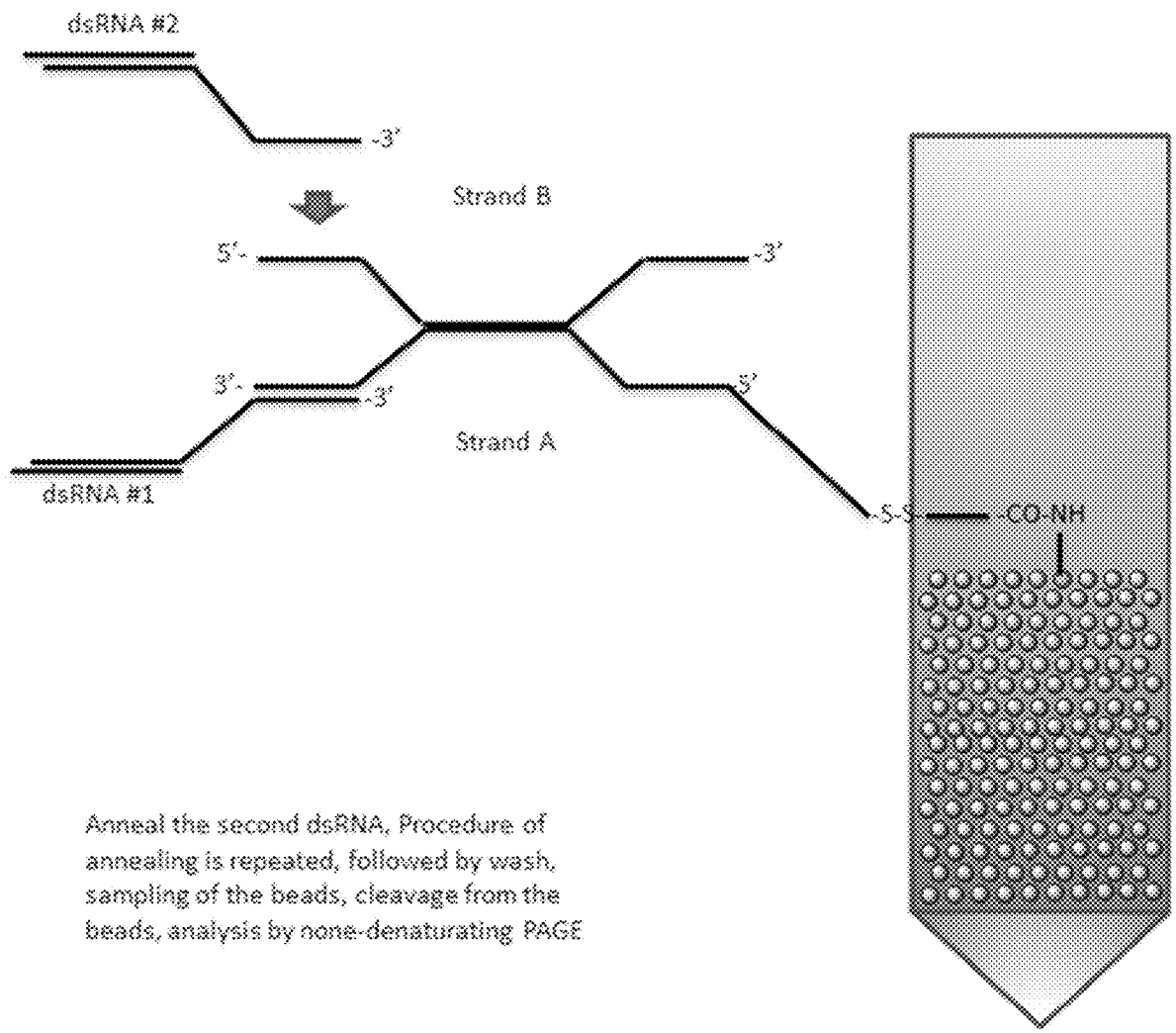
FIG. 11 is a schematic showing the annealing of a second moiety to an exemplary double stranded oligonucleotide or tetravalent core through the nucleic acid overhang on the second moiety to the second functional overhang on the tetravalent core.
Figure 12:
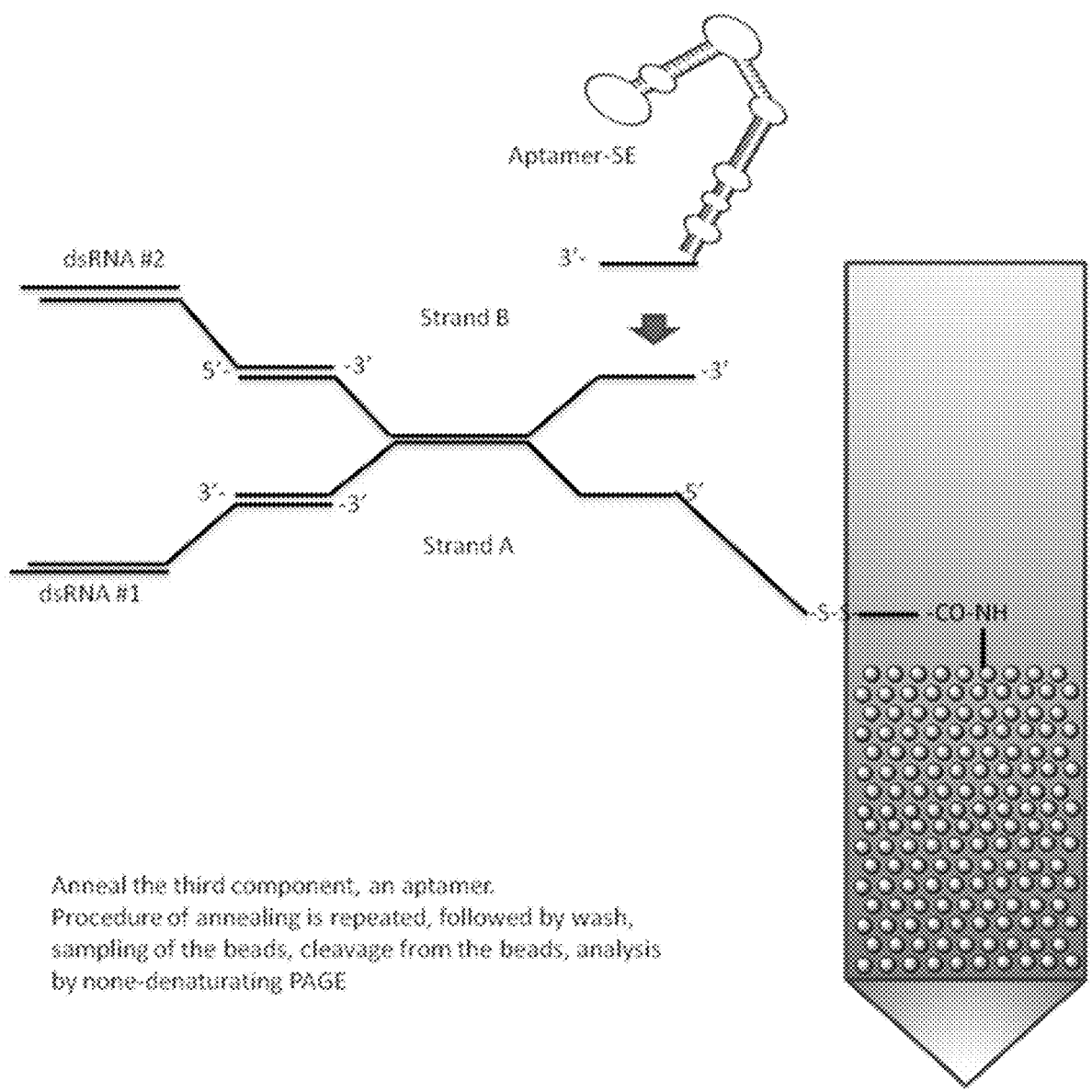
FIG. 12 is a schematic showing the annealing of a third moiety to an exemplary double stranded oligonucleotide or tetravalent core through the nucleic acid overhang on the third moiety to the third functional overhang on the tetravalent core.
Figure 13:
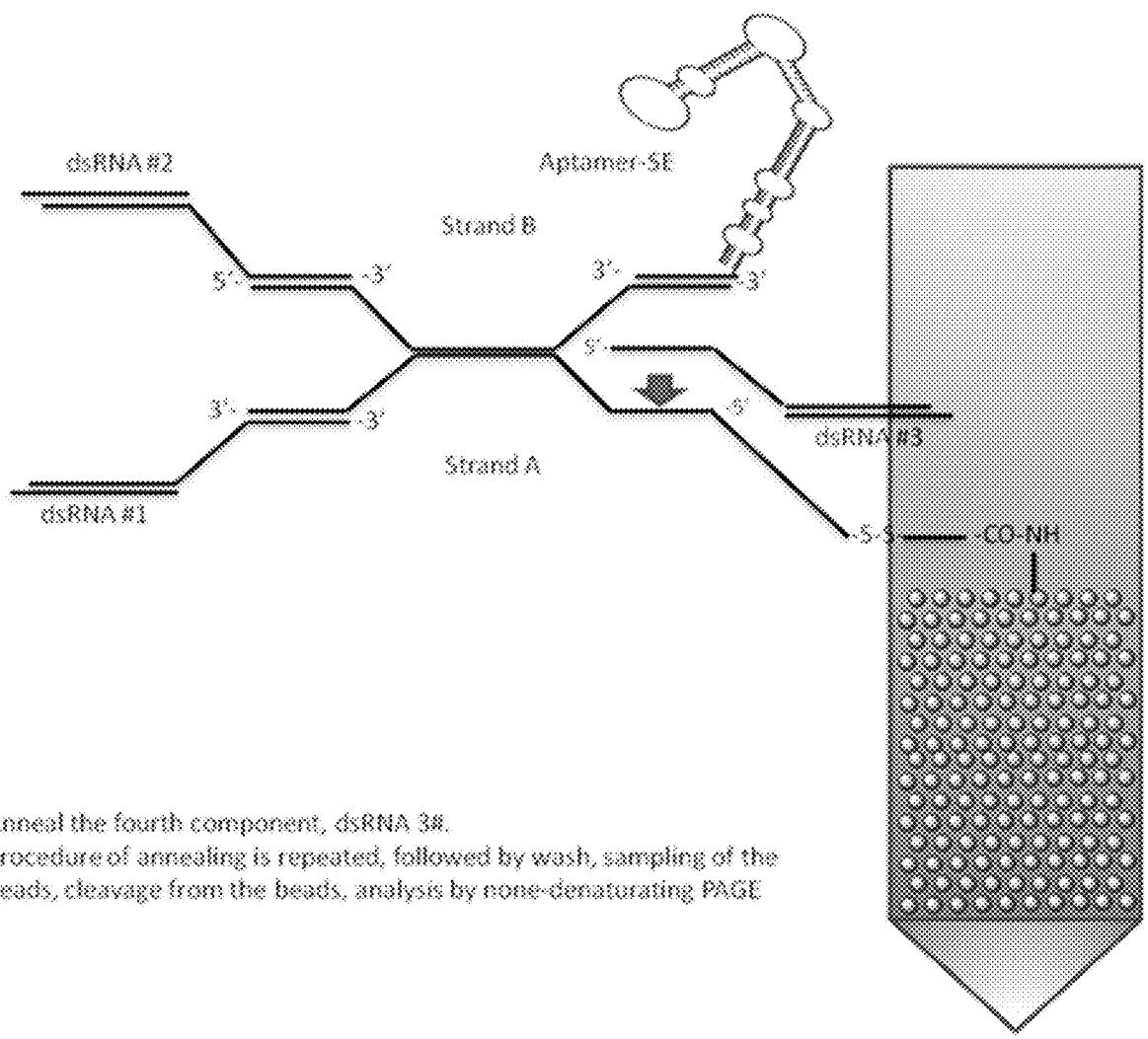
FIG. 13 is a schematic showing the annealing of a fourth moiety to an exemplary double stranded oligonucleotide or tetravalent core through the nucleic acid overhang on the fourth moiety to the fourth functional overhang on the tetravalent core.
Figure 14:
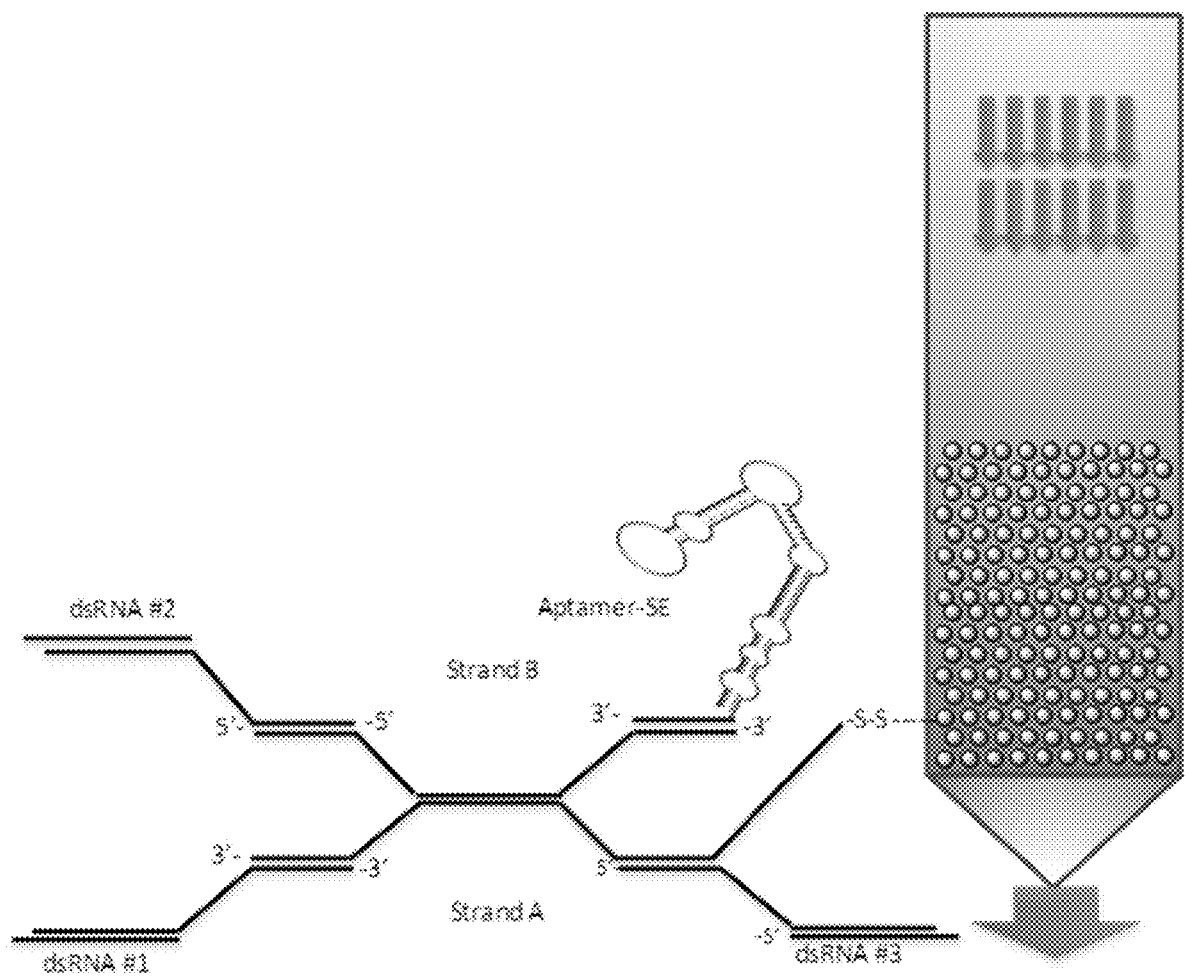
FIG. 14 is a schematic showing an exemplary double stranded oligonucleotide or tetravalent core containing first, second, third, and fourth moieties attached to beads in a column through the cleavable linker on one of the strands of the tetravalent core, e.g., Strand A.
Figure 15:
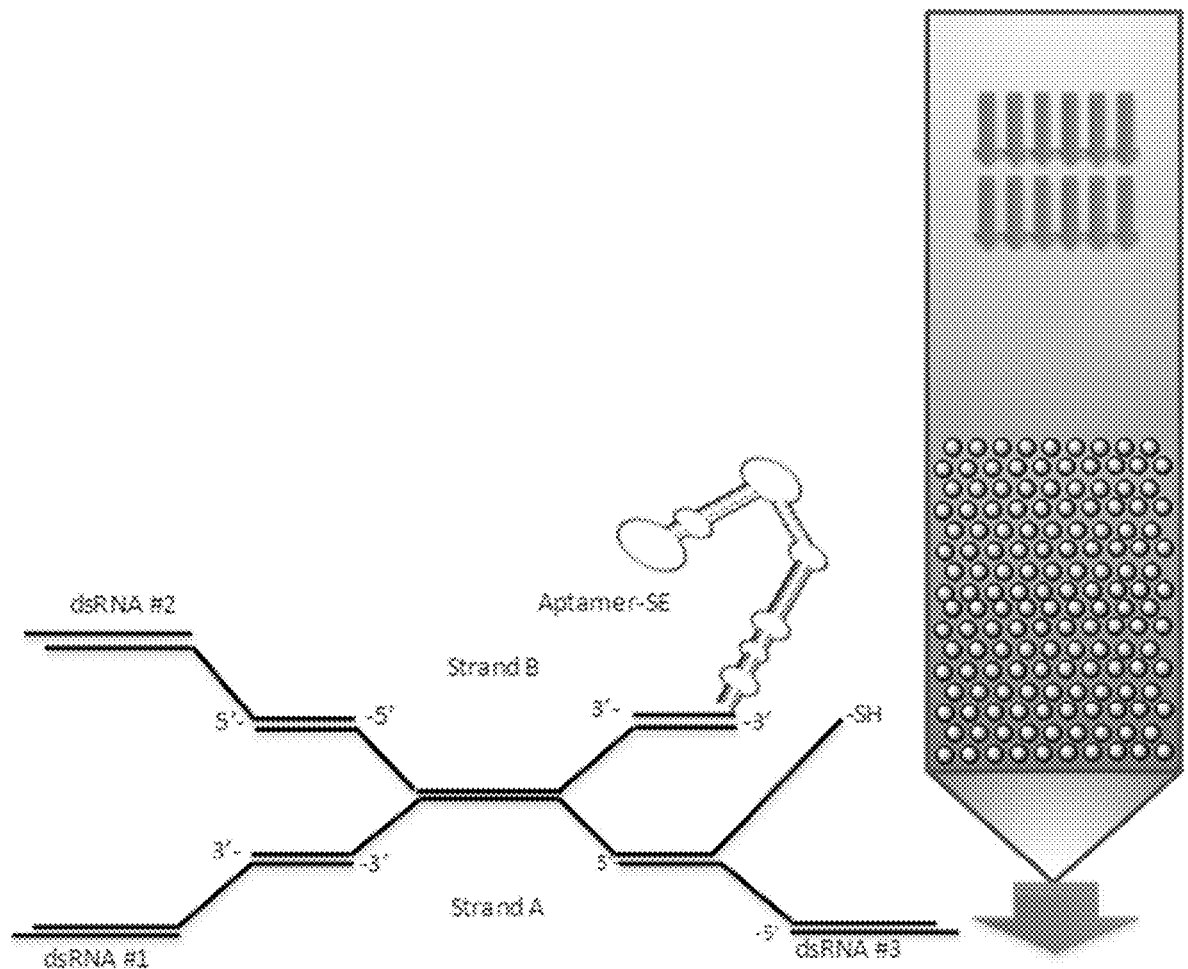
FIG. 15 is a schematic showing the separation of an exemplary double stranded oligonucleotide or tetravalent core containing the first, second, third and fourth moieties from the beads.
Figure 16:
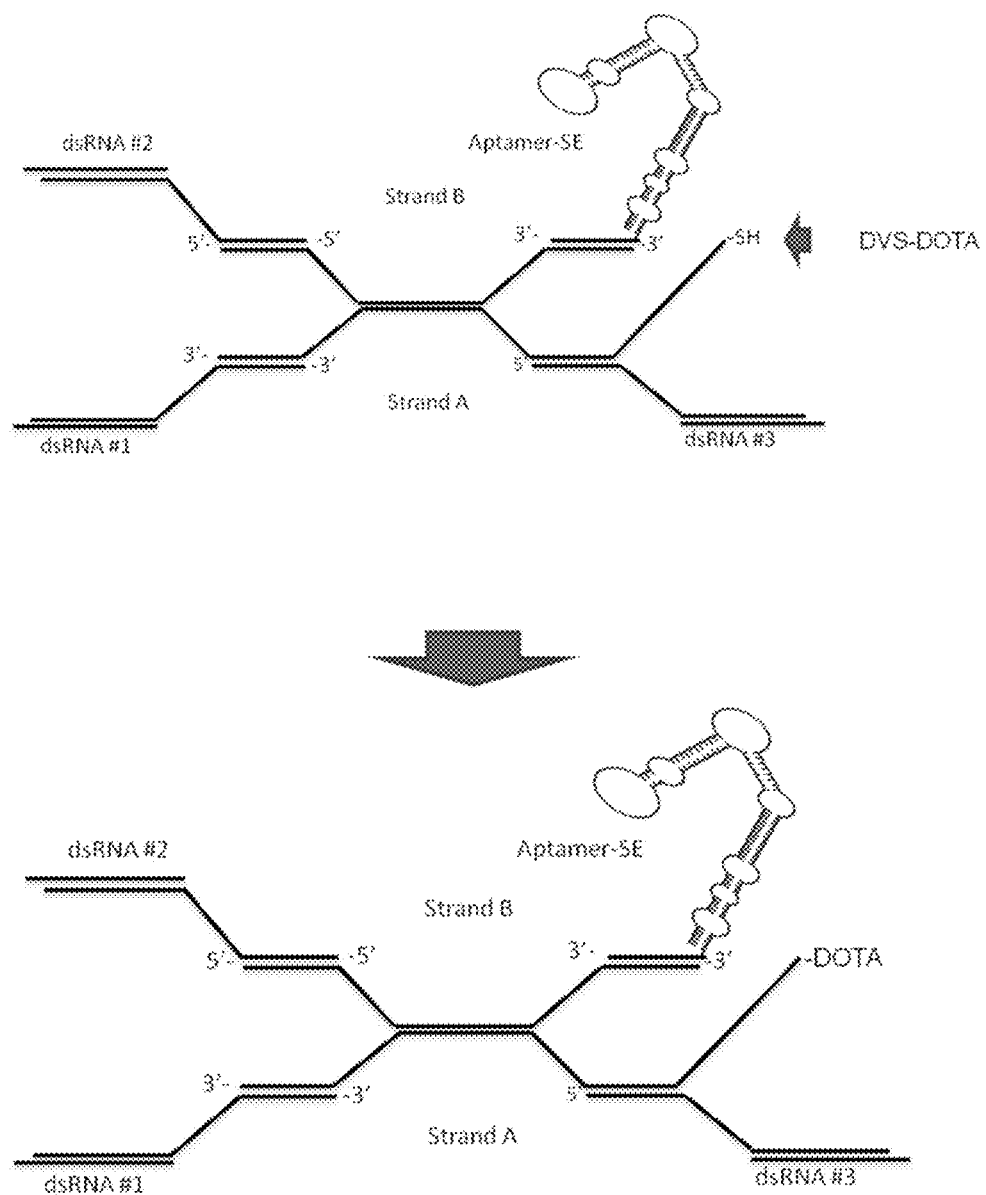
FIG. 16 is a schematic showing the optional attachment of a fifth moiety to the free sulfydryl group on one of the strands of the tetravalent core.

Example 2. Method of Making Multifunctional, Self-Assembling, Customizable Double Stranded Oligonucleotide Molecules A method for making the double stranded oligonucleotide molecules containing one or more moieties was designed. The method is shown in FIGS. 5-16. Briefly, the method involves synthesizing a first strand of the tetravalent core (e.g., Strand A) with a 3' terminal amino group and a cleavable linker, e.g. a disulfide bond (FIG. 5). The first strand is attached to a bead through the cleavable linker (FIG. 6). The beads containing strand A are placed in a column (FIG. 7). An excess of a second strand, e.g., Strand B, is circulated through the column to facilitate the annealing between the first and second strands (FIG. 8). After annealing is complete, the solution containing the excess of Strand B is removed and the column is washed until the eluant is UV clean (FIG. 9). A sample of beads is collected and treated with dithiothreitol (DTT) in order to separate the annealed strands or tetravalent core from the support. The sample is analyzed by polyacrylamide gel electrophoresis (PAGE) in order to verify the completion of the annealing. If annealing is not complete, the column is treated with excess of Strand B again (FIG. 9). After assembly of the tetravalent core is complete, the first moiety is attached by annealing through one of the single-stranded functional oligonucleotides on the core and a single-stranded oligonucleotide attached to the moiety. An excess of the first moiety (e.g., a dsRNA) is added to the column. The solution is circulated through the column until annealing between the first moiety and the core is complete (FIG. 10). Next, the column is washed until UV clean. A sample of beads is collected and treated with DTT in order to separate the core containing the first moiety from the support. Next, the sample is analyzed by PAGE in order to verify the completion of the annealing of the first moiety to the core. If annealing is not complete, the column is treated with excess of the first moiety again (FIG. 10). After annealing of the first moiety to the tetravalent core is complete, the second moiety is attached by annealing again through the nucleic acid overhangs. Briefly, an excess of the second moiety (dsRNA#2) is added to the column. The solution is circulated through the column until annealing is complete. Next, the column is washed until UV clean. A sample of beads is collected and treated with DTT in order to separate the tetravalent core with the first and second moieties from the support. Next, the sample is analyzed by PAGE in order to verify the completion of the annealing of the second moiety. If annealing is not complete, the support is treated with excess of second moiety again (FIG. 11). After annealing of the first and second moieties to the tetravalent core is complete, the third moiety is attached by annealing of the nucleic acid overhangs. An excess of the third moiety (Aptamer-SE) is added to the column and the solution is circulated through the column until the annealing is complete. Next, the column is washed until UV clean. A sample of beads is collected and treated with DTT in order to separate the tetravalent core containing the three moieties from the support. Next, the sample is analyzed by PAGE in order to verify the completion of the annealing of the third moiety. If annealing is not complete, the support is treated with excess of third moiety again (FIG. 12). After the annealing of the first, second and third moieties to the tetravalent core is complete, the fourth moiety (dsRNA#3) is circulated through the column until the annealing of the fourth moiety is complete. Next, the column is washed until UV clean. A sample of beads is collected and treated with DTT in order to separate the tetravalent core containing the four moieties from the support. Next, the sample is analyzed by PAGE in order to verify the completion of the annealing of the fourth moiety. If annealing is not complete, the support is treated with excess of the fourth moiety again (FIG. 13). Once the annealing of the first, second, third and fourth moieties to the tetravalent core is complete, it can be released from the beads. FIG. 14 shows the multi-functional, self-assembling, oligonucleotide molecule still covalently attached to the support (FIG. 14). The multi-functional, self-assembling, oligonucleotide molecule is cleaved from the support by the treatment with an excess of DTT or volatile mercaptane. The solution of DTT or volatile mercaptane is circulated through the column until the cleavage is completed. The oligonucleotide molecule product is in the solution. Thus, the oligonucleotide molecule is now separated from the support. The excess of DTT is removed from the solution containing the oligonucleotide molecule by size exclusion filtration or non-denaturating high performance liquid chromatography (HPLC) (FIG. 15). Optionally, the multi-functional, self-assembling, oligonucleotide molecule is then reacted with a fifth moiety (DVS-DOTA). After the reaction is complete, the product is separated from the excess of the fifth moiety by size exclusion filtration or non-denaturating HPLC (FIG. 16).

EMBODIMENTS

Embodiment 1

A double stranded oligonucleotide molecule comprising:

a first oligonucleotide strand comprising a first nucleic acid sequence bound to a second nucleic acid sequence through a first spacer, wherein said second nucleic acid sequence is bound to a third nucleic acid sequence through a second spacer; and a second oligonucleotide strand comprising a fourth nucleic acid sequence bound to a fifth nucleic acid sequence through a third spacer, wherein said fifth nucleic acid sequence is bound to a sixth nucleic acid sequence through a fourth spacer, wherein the second nucleic acid sequence and the fifth nucleic acid sequence are hybridized to form a double stranded nucleic acid core of said double stranded oligonucleotide.

Embodiment 2

The oligonucleotide of embodiment 1, wherein the first and second spacers are chemically identical.

Embodiment 3

The oligonucleotide of embodiment 1 or 2, wherein the third and fourth spacers are chemically identical.

Embodiment 4

The oligonucleotide of embodiment 3, wherein the first, second, third and fourth spacers are the chemically identical.

Embodiment 5

The oligonucleotide of any one of embodiments 1 to 4, wherein the first, second, third and fourth spacers are independently substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heterarylene.

Embodiment 6

The oligonucleotide of any one of embodiments 1 to 5, wherein the first, second, third and fourth spacers are independently substituted or unsubstituted alkylene, or substituted or unsubstituted heteroalkylene.

Embodiment 7

The oligonucleotide of any one of embodiments 1 to 6, wherein the first, second, third and fourth spacers are independently substituted or unsubstituted alkylene.

Embodiment 8

The oligonucleotide of any one of embodiments 1 to 7, wherein the first, second, third and fourth spacers are independently unsubstituted alkylene.

Embodiment 9

The oligonucleotide of any one of embodiments 1 to 8, wherein the first, second, third and fourth spacers are independently unsubstituted C1-C10 alkylene.

Embodiment 10

The oligonucleotide of any one of embodiments 1 to 8, wherein the first nucleic acid sequence, the third nucleic acid sequence, the fourth nucleic acid sequence and the sixth nucleic acid sequence are single stranded.

Embodiment 11

The oligonucleotide of any one of embodiments 1 to 9, further comprising a first moiety attached to the first nucleic acid sequence of the first oligonucleotide.

Embodiment 12

The oligonucleotide of any one of embodiments 1 to 9 or 11, further comprising a second moiety attached to the third nucleic acid sequence of the first oligonucleotide.

Embodiment 13

The oligonucleotide of any one of embodiments 1 to 9, 11 or 12, further comprising a third moiety attached to the fourth nucleic acid sequence of the second oligonucleotide.

Embodiment 14

The oligonucleotide of any one of embodiments 1 to 9 or 11 to 13, further comprising a fourth moiety attached to the sixth nucleic acid sequence of the second oligonucleotide.

Embodiment 15

The oligonucleotide of any one of embodiments 11 to 14, wherein the first moiety comprises a first moiety nucleic acid sequence hybridized to at least a portion of the first nucleic acid sequence.

Embodiment 16

The oligonucleotide of any one of embodiments 12 to 15, wherein the second moiety comprises a second moiety nucleic acid sequence hybridized to at least a portion of the third nucleic acid sequence.

Embodiment 17

The oligonucleotide of any one of embodiments 13 to 16, wherein the third moiety comprises a third moiety nucleic acid sequence hybridized to at least a portion of the fourth nucleic acid sequence.

Embodiment 18

The oligonucleotide of any one of embodiments 14 to 17, wherein the fourth moiety comprises a fourth moiety nucleic acid sequence hybridized to at least a portion of the sixth nucleic acid sequence.

Embodiment 19

The oligonucleotide of any one of embodiments 1 to 18, wherein the nucleic acid sequences in the first, third, fourth and sixth nucleic acid sequences are the same.

Embodiment 20

The oligonucleotide of any one of embodiments 1 to 18, wherein the nucleic acid sequences in the first and sixth nucleic acid sequences are the same.

Embodiment 21

The oligonucleotide of any one of embodiments 1 to 18 or 20, wherein the nucleic acid sequences in the third and fourth nucleic acid sequences are the same.

Embodiment 22

The oligonucleotide of any one of embodiments 11 to 21, wherein the first, second, third or fourth moiety is selected from the group consisting of a small molecule moiety, antibody moiety, polypeptide moiety or oligonucleotide moiety.

Embodiment 23

The oligonucleotide of any one of embodiments 11 to 21, wherein the first, second, third, or fourth moiety is a targeting moiety.

Embodiment 24

The oligonucleotide of embodiment 23, wherein the targeting moiety is an aptamer moiety or a CpG oligodeoxynucleotide moiety.

Embodiment 25

The oligonucleotide of any one of embodiments 11 to 21, wherein the first, second, third, or fourth moiety is an active agent moiety.

Embodiment 26

The oligonucleotide of embodiment 25, wherein the active agent moiety is selected from the group consisting of a polypeptide moiety, an oligonucleotide moiety, a small molecule moiety or an antibody moiety.

Embodiment 27

The oligonucleotide of embodiment 25, wherein the active agent moiety is a double-stranded nucleic acid moiety.

Embodiment 28

The oligonucleotide of embodiment 27, wherein the double stranded moiety is an siRNA moiety.

Embodiment 29

The oligonucleotide of any one of embodiments 13, 14, 17, or 18, wherein the first and second moieties are active agent moieties and the third moiety is a targeting moiety.

Embodiment 30

The oligonucleotide of any one of embodiments 13, 14, 17, or 18, wherein the first and third moieties are active agent moieties and the second moiety is a targeting moiety.

Embodiment 31

A method of making a double stranded oligonucleotide comprising the steps of:
(a) attaching a first oligonucleotide strand to a substrate through a cleavable linker, said first oligonucleotide strand comprising a first nucleic acid sequence bound to a second nucleic acid sequence through a first spacer, wherein said second nucleic acid sequence is bound to a third nucleic acid sequence through a second spacer, and wherein said first nucleic acid sequence is bound to said cleavable linker;
(b) hybridizing a second oligonucleotide strand to said first oligonucleotide strand thereby forming a double stranded oligonucleotide, said second oligonucleotide strand comprising a fourth nucleic acid sequence bound to a fifth nucleic acid sequence through a third spacer, wherein said fifth nucleic acid sequence is bound to a sixth nucleic acid sequence through a fourth spacer, wherein the second nucleic acid sequence and the fifth nucleic acid sequence are hybridized to form a double stranded nucleic acid core of said double stranded oligonucleotide.

Embodiment 32

The method of embodiment 31, wherein the first and second spacers are chemically identical.

Embodiment 33

The method of embodiment 31 or 32, wherein the third and fourth spacers are chemically identical.

Embodiment 34

The method of embodiment 33, wherein the first, second, third and fourth spacers are the chemically identical.

Embodiment 35

The method of any one of embodiments 31 to 34, wherein the first, second, third and fourth spacers are independently substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heterarylene.

Embodiment 36

The method of any one of embodiments 31 to 35, wherein the first, second, third and fourth spacers are independently substituted or unsubstituted alkylene, or substituted or unsubstituted heteroalkylene.

Embodiment 37

The method of any one of embodiments 31 to 36, wherein the first, second, third and fourth spacers are independently substituted or unsubstituted alkylene.

Embodiment 38

The method of any one of embodiments 31 to 37, wherein the first, second, third and fourth spacers are independently unsubstituted alkylene.

Embodiment 39

The method of any one of embodiments 31 to 38, wherein the first, second, third and fourth spacers are independently unsubstituted C1-C10 alkylene.

Embodiment 40

The method of any one of embodiments 31 to 38, wherein the first nucleic acid sequence, the third nucleic acid sequence, the fourth nucleic acid sequence and the sixth nucleic acid sequence are single stranded.

Embodiment 41

The method of any one of embodiments 31 to 40, further comprising attaching a first moiety to the first nucleic acid sequence.

Embodiment 42

The method of any one of embodiments 31 to 41, further comprising attaching a second moiety to the third nucleic acid sequence.

Embodiment 43

The method of any one of embodiments 31 to 42, further comprising attaching a third moiety to the fourth nucleic acid sequence.

Embodiment 44

The method of any one of embodiments 31 to 43, further comprising attaching a fourth moiety to the sixth nucleic acid sequence.

Embodiment 45

The method of any one of embodiments 31 to 44, wherein the first nucleic acid sequence is covalently bound to the cleavable linker.

Embodiment 46

The method of any one of embodiments 31 to 44, wherein the cleavable linker comprises a nucleic acid sequence and the first nucleic acid sequence is bound to the cleavable linker by hybridizing at least a portion of the first nucleic acid sequence to at least a portion of the cleavable linker nucleic acid sequence.

Embodiment 47

The method of any one of embodiments 31 to 46, further comprising cleaving the cleavable linker to release the first oligonucleotide from the substrate.

Embodiment 48

The method of embodiment 47, wherein the cleaving occurs prior to attaching the fourth moiety to the sixth nucleic acid sequence.

Embodiment 49

The method of any one of embodiments 41 to 48, wherein the first moiety comprises a first moiety nucleic acid sequence hybridized to at least a portion of the first nucleic acid sequence.

Embodiment 50

The method of any one of embodiments 42 to 49, wherein the second moiety comprises a second moiety nucleic acid sequence hybridized to at least a portion of the third nucleic acid sequence.

Embodiment 51

The method of any one of embodiments 43 to 50, wherein the third moiety comprises a third moiety nucleic acid sequence hybridized to at least a portion of the fourth nucleic acid sequence.

Embodiment 52

The method of any one of embodiments 44 to 51, wherein the fourth moiety comprises a fourth moiety nucleic acid sequence to at least a portion of the sixth nucleic acid sequence.

Embodiment 53

The method of any one of embodiments 31 to 52, wherein the nucleic acid sequences in the first, third, fourth and sixth nucleic acid sequences are the same.

Embodiment 54

The method of any one of embodiments 31 to 52, wherein the nucleic acid sequences in the first and sixth nucleic acid sequences are the same.

Embodiment 55

The method of any one of embodiments 31 to 52, wherein the nucleic acid sequences in the third and fourth nucleic acid sequences are the same.

Embodiment 56

The method of any one of embodiments 41 to 55, wherein the first, second, third or fourth moiety is selected from the group consisting of a small molecule moiety, antibody moiety, polypeptide moiety or oligonucleotide moiety.

Embodiment 57

The method of any one of embodiments 41 to 55, wherein the first, second, third, or fourth moiety is a targeting moiety.

Embodiment 58

The method of embodiment 57, wherein the targeting moiety is an aptamer moiety or a CpG oligodeoxynucleotide moiety.

Embodiment 59

The method of any one of embodiments 41 to 55, wherein the first, second, third, or fourth moiety is an active agent moiety.

Embodiment 60

The method of embodiment 59, wherein the active agent moiety is selected from the group consisting of a polypeptide moiety, an oligonucleotide moiety, a small molecule moiety or an antibody moiety.

Embodiment 61

The method of embodiment 59, wherein the active agent moiety is a double-stranded nucleic acid moiety.

Embodiment 62

The method of embodiment 61, wherein the double stranded moiety is an siRNA moiety.

Embodiment 63

The method of embodiment 43 or 44, wherein the first and second moieties and active agent moieties and the third moiety is a targeting moiety.

Embodiment 64

The method of embodiment 43 or 44, wherein the first and third moieties are active agent moieties and the second moiety is a targeting moiety.

Embodiment 65

The method of any one of embodiments 31 to 64, wherein the cleavable linker is cleaved by an enzyme, a catalyst, a chemical compound, temperature, electromagnetic radiation or light.

Embodiment 66

The method of any one of embodiments 31 to 64, wherein the cleavable linker comprises a moiety hydrolysable by beta-elimination.

Embodiment 67

The method of any one of embodiments 31 to 64, wherein the cleavable linker comprises a moiety cleavable by acid hydrolysis.

Embodiment 68

The method of any one of embodiments 31 to 64, wherein the cleavable linker comprises a enzymatically cleavable moiety.

Embodiment 69

The method of any one of embodiments 31 to 64, wherein the cleavable linker comprises a photo-cleavable moiety.

What is claimed is:

1. A double stranded oligonucleotide molecule comprising:
    a first oligonucleotide strand comprising a first nucleic acid sequence bound to a second nucleic acid sequence through a first spacer, wherein said second nucleic acid sequence is bound to a third nucleic acid sequence through a second spacer; and
    a second oligonucleotide strand comprising a fourth nucleic acid sequence bound to a fifth nucleic acid sequence through a third spacer, wherein said fifth nucleic acid sequence is bound to a sixth nucleic acid sequence through a fourth spacer,
    wherein the second nucleic acid sequence and the fifth nucleic acid sequence are hybridized to form a double stranded nucleic acid core of said double stranded oligonucleotide, and
    wherein said first oligonucleotide strand is covalently bound to a substrate through a cleavable linker.

2. The oligonucleotide of claim 1, wherein the first and second spacers are chemically identical.

3. The oligonucleotide of claim 1, wherein the first, second, third and fourth spacers are the chemically identical.

4. The oligonucleotide of claim 1, wherein the first, second, third and fourth spacers are independently substituted or unsubstituted alkylene, or substituted or unsubstituted heteroalkylene.

5. The oligonucleotide of claim 1, wherein the first, second, third and fourth spacers are independently unsubstituted alkylene.

6. The oligonucleotide of claim 1, wherein the first, second, third and fourth spacers are independently unsubstituted C1-C10 alkylene.

7. The oligonucleotide of claim 1, wherein the first nucleic acid sequence, the third nucleic acid sequence, the fourth nucleic acid sequence and the sixth nucleic acid sequence are single stranded.

8. The oligonucleotide of claim 1, further comprising a first moiety attached to the first nucleic acid sequence of the first oligonucleotide.

9. The oligonucleotide of claim 8, further comprising a second moiety attached to the third nucleic acid sequence of the first oligonucleotide.

10. The oligonucleotide of claim 9, further comprising a third moiety attached to the fourth nucleic acid sequence of the second oligonucleotide.

11. The oligonucleotide of claim 10, further comprising a fourth moiety attached to the sixth nucleic acid sequence of the second oligonucleotide.

12. The oligonucleotide of claim 1, wherein the nucleic acid sequences in the first, third, fourth and sixth nucleic acid sequences are the same.

13. The oligonucleotide of claim 11, wherein the first, second, third or fourth moiety is selected from the group consisting of a small molecule moiety, antibody moiety, polypeptide moiety or oligonucleotide moiety.

14. The oligonucleotide of claim 11, wherein the first, second, third, or fourth moiety is a targeting moiety.

15. The oligonucleotide of claim 14, wherein the targeting moiety is an aptamer moiety or a CpG oligodeoxynucleotide moiety.

16. The oligonucleotide of claim 11, wherein the first, second, third, or fourth moiety is an active agent moiety.

17. The oligonucleotide of claim 16, wherein the active agent moiety is selected from the group consisting of a polypeptide moiety, an oligonucleotide moiety, a small molecule moiety or an antibody moiety.

18. A method of making a double stranded oligonucleotide comprising the steps of:
(a) attaching a first oligonucleotide strand to a substrate through a cleavable linker, said first oligonucleotide strand comprising a first nucleic acid sequence bound to a second nucleic acid sequence through a first spacer, wherein said second nucleic acid sequence is bound to a third nucleic acid sequence through a second spacer, and wherein said first nucleic acid sequence is covalently bound to said cleavable linker;
(b) hybridizing a second oligonucleotide strand to said first oligonucleotide strand thereby forming a double stranded oligonucleotide, said second oligonucleotide strand comprising a fourth nucleic acid sequence bound to a fifth nucleic acid sequence through a third spacer, wherein said fifth nucleic acid sequence is bound to a sixth nucleic acid sequence through a fourth spacer, wherein the second nucleic acid sequence and the fifth nucleic acid sequence are hybridized to form a double stranded nucleic acid core of said double stranded oligonucleotide.

19. The method of claim 18, wherein the first, second, third and fourth spacers are independently unsubstituted alkylene.

* * * * *

SEQUENCE LISTING

```
<160> NUMBER OF SEQ ID NOS: 10

<210> SEQ ID NO 1
<211> LENGTH: 17
<212> TYPE: RNA
<213> ORGANISM: Artificial Sequence
<220> FEATURE:
<223> OTHER INFORMATION: Synthetic polynucleotide

<400> SEQUENCE: 1
uucacuacgu cacacag                                                    17

<210> SEQ ID NO 2
<211> LENGTH: 17
<212> TYPE: RNA
<213> ORGANISM: Artificial Sequence
<220> FEATURE:
<223> OTHER INFORMATION: Synthetic polynucleotide

<400> SEQUENCE: 2
acacuuagau aguaugg                                                    17

<210> SEQ ID NO 3
<211> LENGTH: 17
<212> TYPE: RNA
<213> ORGANISM: Artificial Sequence
<220> FEATURE:
<223> OTHER INFORMATION: Synthetic polynucleotide

<400> SEQUENCE: 3
guacauucua gauagcc                                                    17

<210> SEQ ID NO 4
<211> LENGTH: 17
<212> TYPE: RNA
<213> ORGANISM: Artificial Sequence
<220> FEATURE:
<223> OTHER INFORMATION: Synthetic polynucleotide

<400> SEQUENCE: 4
cugugugacg uagugaa                                                    17

<210> SEQ ID NO 5
<211> LENGTH: 17
<212> TYPE: RNA
<213> ORGANISM: Artificial Sequence
<220> FEATURE:
<223> OTHER INFORMATION: Synthetic polynucleotide

<400> SEQUENCE: 5
guaauaauga gcgaguc                                                    17

<210> SEQ ID NO 6
<211> LENGTH: 17
<212> TYPE: RNA
<213> ORGANISM: Artificial Sequence
<220> FEATURE:
<223> OTHER INFORMATION: Synthetic polynucleotide

<400> SEQUENCE: 6
ccauacuauc uaagugu                                                    17

<210> SEQ ID NO 7
<211> LENGTH: 22
<212> TYPE: RNA
<213> ORGANISM: Artificial Sequence
```

```
<220> FEATURE:
<223> OTHER INFORMATION: Synthetic polynucleotide

<400> SEQUENCE: 7
cauaaguucc aguuccaaca cg                                              22

<210> SEQ ID NO 8
<211> LENGTH: 17
<212> TYPE: RNA
<213> ORGANISM: Artificial Sequence
<220> FEATURE:
<223> OTHER INFORMATION: Synthetic polynucleotide

<400> SEQUENCE: 8
ggcuaucuag aauguac                                                    17

<210> SEQ ID NO 9
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 9
cguguuggaa cuggaacuua ug                                              22

<210> SEQ ID NO 10
<211> LENGTH: 17
<212> TYPE: RNA
<213> ORGANISM: Artificial Sequence
<220> FEATURE:
<223> OTHER INFORMATION: Synthetic polynucleotide

<400> SEQUENCE: 10
gacucgcuca uuauuac                                                    17
```